United States Patent
Brown et al.

(10) Patent No.: US 6,723,893 B1
(45) Date of Patent: Apr. 20, 2004

(54) MICE HAVING A MUTANT SOD-1-ENCODING TRANSGENE

(75) Inventors: Robert Brown, Needham, MA (US); H. Robert Horvitz, Cambridge, MA (US); Daniel R. Rosen, Dedham, MA (US)

(73) Assignees: Massachusetts Institute of Technology, Cambridge, MA (US); The General Hospital Corporation, Inc., Boston, MA (US)

(*) Notice: Subject to any disclaimer, the term of this patent is extended or adjusted under 35 U.S.C. 154(b) by 1,484 days.

(21) Appl. No.: 08/204,052

(22) Filed: Feb. 28, 1994

Related U.S. Application Data

(63) Continuation-in-part of application No. 08/023,980, filed on Feb. 26, 1993.

(51) Int. Cl.[7] .................... A01K 67/00; A01K 67/033; A01K 67/02; G01N 33/00
(52) U.S. Cl. .................... 800/18; 800/9; 800/3
(58) Field of Search .................... 800/2; 536/23.1

(56) References Cited

U.S. PATENT DOCUMENTS

| | | |
|---|---|---|
| 5,066,591 A | 11/1991 | Hallewell et al. ............ 435/189 |
| 5,084,390 A | 1/1992 | Hallewell et al. ............ 435/188 |
| 5,196,335 A | 3/1993 | Groner .................... 435/240.2 |
| 5,248,603 A | 9/1993 | Marklund et al. ........... 435/189 |

FOREIGN PATENT DOCUMENTS

| | | | |
|---|---|---|---|
| WO | WO 91/04315 | 4/1991 | |
| WO | WO 92/05178 | 4/1992 | ......... C07D/487/22 |

OTHER PUBLICATIONS

Lannfelt et al (1993) Behav. Brain Res. 57, 207–213.*
Mullins et al (1993) Hypertension 22, 630–633.*
Bowling A.C. et al. "Superoxide Dismutase Activity, Oxidative Damage, And Mitochondrial Energy Metabolism in Familial And Sporadic Amyotrophic Lateral Sclerosis." Journal of Neurochemistry 61:2322–2325, 1993.
Ceballos, I. et al. "Localization of copper–zinc superoxide dismutase mRNA in human hippocampus by in situ hybridization." Neuroscience Letters 105:41–46, 1989.
Cho J. & Yang, J. "Human superoxidedismutase gene preparation—by cloning cDNA, chemical synthesis and mutation." Derwent Publications Ltd., London, GB; AN 93–083393.
Eisen A. & Krieger C. "Pathogenic mechanisms in sporadic amyotrophic lateral sclerosis." Canadian Journal of Neurological Sciences 20:286–296, 1993.
Yim, M.B. et al. "Enzyme function of copper, zinc superoxidedismutase as a free radical generator." Journal of Biological Chemistry 268:4099–4105, 1993.
Brock et al., The Lancet, vol. 342, Issued Oct. 23, 1993, pp. 1050–1051.

Ogasawara et al., Nature Genetics, vol. 5, Issued Dec. 1993, pp. 323–324.

Rosen et al., Nature, vol. 362, Issued Mar. 4, 1993, pp. 59–62.

Beckman et al., "Apparent hydrozyl radical production by peroxynitrite: Implications for endothelial injury from nitric oxide and superoxide", PNAS USA 87:1620–1624, 1990.

Chang et al., "Genetic and Biochemical Characterization of Cu, Zn Superoxide Dismutase Mutants in *Saccharomyces cerevisiae*" J. Biological Chemistry 266:4417–4424, 1991.

Crapo et al., "Copper, zinc superoxide dismutase is primarily a cytosolic protein in human cells" PNAS USA 89:10405–10409, 1992.

Djinovic et al., "Crystal Structure of Yeast Cu, Zn Superoxide Dismutase", J. Molecular Biology, 225:791–809, 1992.

Elroy–Stein et al., "Overproduction of human Cu/Zn–superoxide dismutase in transfected cells: extenuation of paraquat–mediated cytotoxicity and enhancement of lipid peroxidation", EMBO Journal, 5:615–622, 1986.

Epstein et al., "Transgenic mice with increased Cu/Zn–superoxide dismutase activity: Animal model of dosage effects in Down syndrome", PNAS USA 84:8044–8048, 1987.

Hallewell et al., "Thermostabilization of Recombinant Human and Bovine CuZn Superoxide Dismutases by Replacement of Free Cysteines", Biochem. Biophys. Research Comm., 181:474–480, 1991.

Jabusch et al., "Some Sulfhydryl Properties and Primary Structure of Human Erythrocyte Superoxide Dismutase", Biochemistry 19:2310–2316, 1980.

Kirby et al., "A Picomolar Spectrophotometric Assay for Superoxide Dismutase", Analyt. Biochemistry 127:435–440, 1982.

Krall et al., "Superoxide Mediates the Toxicity of Paraquat for Cultured Mammalian Cells", J. Biological Chemistry, 263:1910–1914, 1988.

Leopock et al., "Contribution of Conformational Stability and Reversibility of Unfolding to the Increased Thermostability of Human and Bovine Superoxide Dismutase Mutated at Free Cysteines", J. Biol. Chem. 265:216 21612–21618, 1990.

(List continued on next page.)

*Primary Examiner*—Deborah Crouch
(74) *Attorney, Agent, or Firm*—Clark & Elbing, LLP; Kristina Bieker-Brady

(57) ABSTRACT

Disclosed is the family of genes responsible for the neurodegenerative diseases, particularly Amyotrophic Lateral Sclerosis. Methods and compounds for the diagnosis, prevention, and therapy of the disease are also disclosed.

17 Claims, 17 Drawing Sheets

OTHER PUBLICATIONS

Lieman–Hurwitz et al., "Human cytoplasmic superoxide dismutase cDNA clone: A probe for studying the molecular biology of Down syndrome", PNAS USA, 79:2808–2811, 1982.

Malinowski et al., "Subunit Association and Side–Chain Reactivities of Bovine Erythrocyte Superoxide Superoxide Dismutase in Denaturing Solvents", Biochemistry 18:5055–5060, 1979.

Misra et al., "Superoxide Dismutase: "Positive" Spectrophotometric Assays", Analyt. Biochemistry, 79:553–560, 1977.

Oyanagui, "Reevaluation of Assay Methods and Establishment of Kit for Superoxide Dismutase Activity", Analyt. Biochemistry, 290–296, 1984.

Parge et al., "Atomic structures of wild–type and thermostable mutant recombinant human Cu,Zn superoxide dismutase", PNAS USA, 89:6109–6113, 1992.

Parge et al., "Crystallographic Characterization of Recombinant Human CuZn Superoxide Dismutase", J. Biological Chem., 261:16215–16218, 1986.

Sawada et al., "One–Electron Transfer Reactions in Biochemical Systems", Biochem. Biophys. Acta 327: 257–265, 1973.

Sherman et al., "Nucleotide sequence and expression of human chromosome 21–encoded superoxide dismutase mRNA" PNAS USA, 80:5465–5469, 1983.

Sherman et al., "Human Cu/Zn superoxide dismutase gene: molecular characterization of its two mRNA species", 12:9349–9365, 1984.

Spitz et al., "An Assay for Superoxide Dismutase Activity in Mammalian Tissue Homogenates", Analyt. Biochem. 179:8–18, 1989.

Beauchamp, C., et al., "Superoxide Dismutase: Improved Assays and an Assay Applicable to Acrylamide Gel," *Analytical Biochemistry*, 44: 276 (1971).

Beckman, J.S., et al., "Superoxide Dismutase and Catalase Conjugated to Polyethylene Glycol Increases Endothelial Enzyme Activity and Oxidant Resistance," *J. of Biological Chemistry*, 263:6884 (1988).

Bracco, F., et al., "Determination of Superoxide Dismutase Activity by the Polarographic Method of Catalytic Currents in The Cerebrospinal Fluid of Aging Brain and Neurologic Degenerative Diseases," *Superoxide Dismutase in CSF*, 196:36 (1990).

Carlioz, A., et al., "Isolation of superoxide dismutase mutants in *Escherichia coli*: is superoxide dismutase necessary for aerobic life?" *EMBO Journal*, 5:623 (1986).

Deng, H., "Amyotrophic Lateral Sclerosis and Structural Defects in Cu, Zn Superoxide Dismutase" *Science*, 261:1047 (1993).

Hallewell, R.A., et al., "Structure of the Human Cu/Zn SOD Gene," *Superoxide and Superoxide Dismutase* in Chemistry, Biology and Medicine, p. 249 (1986).

Halliwell, B., "Oxidants and human disease: some new concepts," *FASEB Journal*, 1:358 (1987).

Hartmann, H.A., et al., "Deficiency of Copper Can Cause Neuronal Degeneration," *Medical Hypotheses*, 38:75 (1992).

Hjalmarsson, K., et al., "Isolation and sequence of complementary DNA encoding human extracellular superoxide dismutase," *Proc. Natl. Acad. Sci. USA*, 84:6340 (1987).

Huang, T.T., et al., "Relationship of resistance to oxygen free radicals to CuZn–superoxide dismutase activity in transgenic, transfected, and trisomic cells," *FASEB Journal*, 6:903 (1992).

Hudson, A.J. "Amyotrophic Lateral Sclerosis and its Associations with Dementia, Parkinsonism and other Neurological Disorders: A Review," *Brain*, 104:217 (1981).

Imlay, J.A., et al. "Toxic DNA Damage by Hydrogen Peroxide Through the Fenton Reaction in Vivo and in Vitro," *Science*, 240:640 (1988).

Levanon, D., et al., "Architecture and anatomy of the chromosomal locus in human chromosome 21 encoding the Cu/Zn superoxide dismutase," *EMBO Journal*, 4:77 (1985).

Liu, T.H., et al., Polyethylene glycol–conjugated superoxide dismutase and catalase reduce ischemic brain injury, *American Journal of Physiology*, 256:589 (1989).

McCord, J.M, et al., "Superoxide Dismutase, An Enzymic Function for Erythrocuprein (Hemocuprein)," *Journal of Biological Chemistry*, 244:6049 (1969).

Olanow, C.W., "An Introduction to the Free Radical Hypothesis in Parkinson's Disease," *Annals of Neurology*, 32:s2 (1992).

Oury, T.D., et al., "Extracellular superoxide dismutase, nitric oxide, and central nervous system $O_2$ toxicity," *Proc. Natl. Acad. Sci. USA*, 89:9715 (1992).

Siddique, T., et al., "Linkage of a Gene Causing Familial Amyotrophic Lateral Sclerosis to Chromosome 21 and Evidence of Genetic–Locus Heterogeneity," *New England Journal of Medicine*, 324:1381 (1991).

Wispé, J.R., et al., "Synthesis and processing of the precursor for human mangano–superoxide dismutase," *Biochimica et Biophysica Acta*. 994:30 (1989).

\* cited by examiner

Exon 2

Exon 4

Fig.1C-1

Exon 2

```
                                       S D         R
                               R V L T E G D   H G F H V H E F G D N T A
FALS          E S N G P V K V W G S I K G L T E G D H G F H V H E F G D N T A   SEQ ID NO: 15
human         . G D T T V L V V T G T I T K G L T E G D H G F H V H Q F G D N T Q   SEQ ID NO: 16
cow           G E K . E P V . . T G T I T K G L T P G D H G F H V H Q F G D N T Q   SEQ ID NO: 17
pig           A S G E P V . . A V T G S I Q G L T P G D H G F H V H Q F G D N T Q   SEQ ID NO: 18
mouse         G N A N A . . V K G S I L K G L T P G D H G F H V H E F G D N T N   SEQ ID NO: 19
swordfish     S S G T P V . . V G K G E V T G L T P A K H G F H I H Q F G D N T N   SEQ ID NO: 20
Drosophila    K E G L P T T . V K T G E V K G L T P G L H G F H L H E Y G D T T N   SEQ ID NO: 21
Onchocerca    G V A . P T T T . V G N I S G L T P G L H G F H L H Q F G D T T N   SEQ ID NO: 22
tomato        D D G . P T T V T Y N V R I S G L A P G L H G F H L H A L G D T T N   SEQ ID NO: 23
spinach       S E S E P T T V S Y E I A G N S P N A E R G F H I H E F G D A T N   SEQ ID NO: 24
                          3 3       4 1                         4 3
                          7 8
```

Fig.1C-2

Exon 4

```
                      R           C A           G           V
                              D G V A D         I E D       S L S G D H
FALS          H V G D L G N V T A D K D G V A D V S I E D S V I S L S G D H C I I G R T L V   SEQ ID NO: 25
human         H V G D L G N V T A D K D G V A D V S I E D S V I S L S G D H C I I G R T L V   SEQ ID NO: 26
cow           H V G D L G N V T A D K N G V A D V S I E D R V I S L S G E Y S I I G R T M V   SEQ ID NO: 27
pig           H V G D L G N V T A G K D G V A N V S I E D R V I A L S G D H S I I G R T M V   SEQ ID NO: 28
mouse         H V G D L G N V T A D A N G V A K I D I T T D S K K I S L T L F G A D S I I G R T M V   SEQ ID NO: 29
swordfish     H L G D L G N I E A T G D C P T K V N I S T D D Q H I Q L L G P Y S I I G R T V V   SEQ ID NO: 30
Drosophila    H V G D L G N I E A G A D G T A H I S I T D D S K K I T L F G A D S N I I G R T V V   SEQ ID NO: 31
Onchocerca    E A G D L G N I T V G E D G T A S F T I T D D K I Q L L G P N S I I G R S I V   SEQ ID NO: 32
tomato        H A G D L G N I V A N T D G V A E A T I H D N Q I P L T G P N S V V G R A L V   SEQ ID NO: 33
spinach       H V G D M G N V K T D E N G V A K G S F K D S L I K L I G P T S V V G R S V V   SEQ ID NO: 34
              8 5       9 3                 1 0 0     1 0 6                       1 1 3
```

```
-552 GAATTCTGCC AACCAAATAA GAAACTCTAT ACTAAGGACT AAGAAAATTG

-502 CAGGGGAAGA AAAGGTAAGT CCCGGGATTG AGGTGTAGCG ACTTTCTATA

-452 CCCTCAGAAA ACTAAAAAAC AAGACAAAAA AATGAAAACT ACAAAAGCAT

-402 CCATCTTGGG GCGTCCCAAT TGCTGAGTAA CAAATGAGAC GCTGTGGCCA

-352 AACTCACGTC ATAACTAATG ACATTTCTAG ACAAAGTGAC TTCAGATTTT

-302 CAAAGCGTAC CCTGTTTACA TCATTTTGCC AATTTCGCGT ACTGCAACCG

-252 GCGGGCCACG CCCCCGTGAA AAGAAGGTTG TTTTCTCCAC ATTTCGGGGT

-202 TCTGGACGTT TCCCGGCTGC GGGGCGGGGG GAGTCTCCGG CGCACGCGGC

-152 CCCTTGGCCC CGCCCCCAGT CATTCCCGGC CACTCGCGAC CCGAGGCTGC

-102 CGCAGGGGGC GGGCTGAGCG CGTGCGAGGC GATTGGTTTG GGCCAGAGT

-52 GGGCGAGGCG CGGAGGTCTG GCCTATAAAG TAGTCGCGGA GACGGGGTGC

-2 TG

1 GTTTGCGTCG TAGTCTCCTG CAGCGTCTGG GGTTTCCGTT GCAGTCCTCG

51 GAACCAGGAC CTCGGCGTGG CCTAGCGAGT T ATG GCG ACG AAG GCC
                                     met ala thr lys ala 97 GTG TGC GTG CTG AAG GGC GAC GGC CCA GTG CAG GGC ATC ATC
  6 val cys val leu lys gly asp gly pro val gln gly ile ile 139 AAT TTC GAG CAG AAG      GCAAGGG CTGGGACGGG AGGCTTGTGG
 20 asn phe glu gln lys     intron 1

TTGCGAGGCC GCTCCCGACC CGCTCGTCCC CCCGCGACCC TTTGCATGGA

CGGGTCGCCC GCCAGGG............................

CCTAGAGCAG GTTAAGCAGC TTGCTGGAGG TTCACTGGCT AGAAAGTGGT

CAGCCTGGGA TTTGGACACA GATTTTTCCA CTCCCAAGTC TGGCTGCTTT

TTACTTCACT GTGAGGGGTA AAGGTAAATC AGCTGTTTTC TTTGTTCAGA

AACTCTCTCC AACTTTGCAC TTTTCTTAAA G
```

FIG. 2-1

```
154 GAA AGT AAT GGA CCA GTG AAG GTG TGG GGA AGC ATT AAA GGA
 26 glu ser asn gly pro val lys val trp gly ser ile lys gly 196 CTG ACT GAA GGC CTG CAT GGA TTC CAT GTT CAT GAG TTT GGA
 40 leu thr glu gly leu his gly phe his val his glu phe gly 238 GAT AAT ACA GCA G        GTCGGGTGTT.....................
 54 asp asn thr ala          intron 2

GTGTTTCTTT TTAGAATGTA TTTGGGAACT TTAATTCATA ATTTAGCTTT

TTTTTCTTCT TCTTATAAAT AG

251 GC TGT ACC AGT GCA GGT CCT CAC TTT AAT CCT CTA TCC AGA
 58 gly cys thr ser ala gly pro his phe asn pro leu ser arg 292 AAA CAC GGT GGG CCA AAG GAT GAA GAG AG    GTAACAAGAT
 72 lys his gly gly pro lys asp glu glu arg   intron 3

GCTTAACTCT TGTAATAATg gccGATCATG gTTCTGGAGT TCATATGGTA

TACTACTTGT AAATATGTGC TAAGATAATT CCGTGTTTCC CCCACCTTTG

CTTTTGAACT TGCTGACTCA TCTAAACCCT GCTCCCAAAT GCTGGAATGC

TTTTACTTCC TGGGCTTAAA GGAATTGACA AATGGGCACT TAAAACGATT

TGGTTTTGTA GCATTTGATT GAATATAGAA CTAATACAAG TGCCAAAGGG

GAACTAATAC AGGAAATGTT CATGAACAGT ACTGTCAACC ACTAGCAAAA

TCAATCATCA TT..............................

GTACTTCTGA AATCAGGTGC AGCCCCATCT TTCTTCCCAG AGCATTAGTG

TGTAGACGTG AAGCCTTGTT TGAAGAGCTG TATTTAGAAT GCCTAGCTAC

TTGTTTGCAA ATTTGTGTCC TACTCAGTCA AGTTTTAATT TAGCTCATGA

ACTACCTTGA TGTTTAGTGg CATCAGCCCT AATCCATCTG ATGCTTTTTC

ATTATTAG

321   G CAT GTT GGA GAC TTG GGC AAT GTG ACT GCT GAC AAA GAT
 82     his val gly asp leu gly asn val thr ala asp lys asp 361 GGT GTG GCC GAT GTG TCT ATT GAA GAT TCT GTG ATC TCA CTC
 95 gly val ala asp val ser ile glu asp ser val ile ser leu 403 TCA GGA GAC CAT TGC ATC ATT GGC CGC ACA CTG GTG
109 ser gly asp his cys ile ile gly arg thr leu val
```

FIG. 2-2

```
            GTAAG TTTTCATAAA AGGATATGCA TAAAACTTCT TCTAACATAC
         intron 4

AGTCATGTAT CTTTTCACTT TGATTGTTAG TCGCGGTTTC TAAGATCCAG

ATAAACTGT........................................

GAAAAAGCTT TGAGTAGTAG TTTCTACTTT TAAACTACTA AATATTAGTA

TATCTCTCTA CTAGGATTAA TGTTATTTTT CTAATATTAT GAGGTTCTTA

AACATCTTTT GGGTATTGTT GGGAGGAGGT AGTGATTACT TGACAGCCCA

AAGTTATCTT CTTAAAATTT TTTACAG

444 GTC CAT GAA AAA GCA GAT GAC TTG GGC AAA GGT GGA AAT GAA
 121 val his glu lys ala asp asp leu gly lys gly gly asn glu 486 GAA AGT ACA AAG ACA GGA AAC GCT GGA AGT CGT TTG GCT TGT 135
glu ser thr lys thr gly asn ala gly ser arg leu ala cys 528 GGT GTA ATT GGG ATC GCC CAA TAA   ACATTCCCT TGGATGTAGT
 149 gly val ile gly ile ala gln

CTGAGGCCCC TTAACTCATC TGTTATCCTG CTAGCTGTAG AAATGTATCC

TGATAAACAT TAAACACTGT AATCTTAAAA GTGTAATTGT GTGACTTTTT

CAGAGTTGCT TTAAAGTACC TGTAGTGAGA AACTGATTTA TGATCACTTG

GAAGATTTGT ATAGTTTTAT AAAACTCAGT TAAAATGTCT GTTTCAATGA

CCTGTATTTT GCCAGACTTA AATCACAGAT GGGTATTAAA CTTGTCAGAA

TTTCTTTGTC ATTCAAGCCT GTGAATAAAA ACCCTGTATG GCACTTATTA

TGAGGCTATT AAAAGAATCC AAATTCAAAC TAAATTAGCT CTGATACTTA

TTTATATAAA CTGCTTCAGT GGAACAGATT TAGTAATACT AACAGTGATA

GCATTTTATT TTGAAAGTGT TTTGAGACCA TCAAAATGCA TACTTTAAAA

CAGCAGGTCT TTTAGCTAAA ACTAACACAA CTCTGCTTAG ACAAATAGGC

TGTCCTTTGA AGCTT    SEQ ID NO: 1
```

FIG. 2-3

```
  1  CCGCCGGCGC GCAGGAGCGG CACTCGTGGC TGTGGTGGCT TCGGCAGCGG

51  CTTCAGCAGA TCGGCGGCAT CAGCGGTACG ACCAGCACTA GCAGC    ATG
                                                          met 99  TTG AGC CGG GCA GTG TGC GGC ACC AGC AGG CAG CTG GCT CCG
     leu ser arg ala val cys gly thr ser arg gln leu ala pro 141  GCT TTG GGG TAT CTG GGC TCC AGG CAG AAG CAC AGC CTC CCC
     ala leu gly tyr leu gly ser arg gln lys his ser leu pro 183  GAC CTG CCC TAC GAC TAC GGC GCC CTG GAA CCT CAC ATC AAC
     asp leu pro tyr asp tyr gly ala leu glu pro his ile asn 225  GCG CAG ATC ATG CAG CTG CAC CAC AGC AAG CAC CAC GCG GCC
     ala gln ile met gln leu his his ser lys his his ala ala 267  TAC GTG AAC AAC CTG AAC GTC ACC GAG GAG AAG TAC CAG GAG
     tyr val asn asn leu asn val thr glu glu lys tyr gln glu 309  GCG TTG GCA AAG GGA GAT GTT ACA GCC CAG ACA GCT CTT CAG
     ala leu ala lys gly asp val thr ala gln thr ala leu gln 351  CCT GCA CTG AAG TTC AAT GGT GGT GGT CAT ATC AAT CAT AGC
     pro ala leu lys phe asn gly gly gly his ile asn his ser 393  ATT TTC TGG ACA AAC CTC AGC CCT AAC GGT GGT GGA GAA CCC
     ile phe trp thr asn leu ser pro asn gly gly gly glu pro 435  AAA GGG GAG TTG CTG GAA GCC ATC AAA CGT GAC TTT GGT TCC
     lys gly glu leu leu glu ala ile lys arg asp phe gly ser 477  TTT GAC AAG TTT AAG GAG AAG CTG ACG GCT GCA TCT GTT GGT
     phe asp lys phe lys glu lys leu thr ala ala ser val gly 519  GTC CAA GGC TCA GGT TGG GGT TGG CTT GGT TTC AAT AAG GAA
     val gln gly ser gly trp gly trp leu gly phe asn lys glu 561  CGG GGA CAC TTA CAA ATT GCT GCT TGT CCA AAT CAG GAT CCA
     arg gly his leu gln ile ala ala cys pro asn gln asp pro 603  CTG CAA GGA ACA ACA GGC CTT ATT CCA CTG CTG GGG ATT GAT
     leu gln gly thr thr gly leu ile pro leu leu gly ile asp 645  GTG TGG GAG CAC GCT TAC TAC CTT CAG TAT AAA AAT GTC AGG
     val trp glu his ala tyr tyr leu gln tyr lys asn val arg 687  CCT GAT TAT CTA AAA GCT ATT TGG AAT GTA ATC AAC TGG GAG
     pro asp tyr leu lys ala ile trp asn val ile asn trp glu 729  AAT GTA ACT GAA AGA TAC ATG GCT TGC AAA AAG TAA  ACCACG
     asn val thr glu arg tyr met ala cys lys lys

771  ATCGTTATGC TGAGTATGTT AAGCTCTTTA TGACTGTTTT TGTAGTGGTA
```

FIG. 3-1

```
821  TAGAGTACTG CAGAATACAG TAAGCTGCTC TATTGTAGCA TTTCTTGATG
871  TTGCTTAGTC ACTTATTTCA TAAACAACTT AATGTTCTGA ATAATTTCTT
921  ACTAAACATT TTGTTATTGG GCAAGTGATT GAAAATAGTA AATGCTTTGT
971  GTGATTG      SEQ ID NO: 2
```

FIG. 3-2

```
  1  CTGGGTGCAG CTCTCTTTTC AGGAGAGAAA GCTCTCTTGG AGGAGCTGGA

51  AAGGTGCCCG ACTCCAGCC      ATG CTG GCG CTA CTG TGT TCC TGC
                                met leu ala leu leu cys ser cys 94  CTG CTC CTG GCA GCC GGT GCC TCG GAC GCC TGG ACG GGC GAG
     leu leu leu ala ala gly ala ser asp ala trp thr gly glu 136  GAC TCG GCG GAG CCC AAC TCT GAC TCG GCG GAG TGG ATC CGA
     asp ser ala glu pro asn ser asp ser ala glu trp ile arg 178  GAC ATG TAC GCC AAG GTC ACG GAG ATC TGG CAG GAG GTC ATG
     asp met tyr ala lys val thr glu ile trp gln glu val met 220  CAG CGG CGG GAC GAC GAC GGC ACG CTC CAC GCC GCC TGC CAG
     gln arg arg asp asp asp gly thr leu his ala ala cys gln 262  GTG CAG CCG TCG GCC ACG CTG GAC GCC GCG CAG CCC CGG GTG
     val gln pro ser ala thr leu asp ala ala gln pro arg val 304  ACC GGC GTC GTC CTC TTC CGG CAG CTT GCG CCC CGC GCC AAG
     thr gly val val leu phe arg gln leu ala pro arg ala lys 346  CTC GAC GCC TTC TTC GCC CTG GAG GGC TTC CCG ACC GAG CCG
     leu asp ala phe phe ala leu glu gly phe pro thr glu pro 388  AAC AGC TCC AGC CGC GCC ATC CAC GTG CAC CAG TTC GGG GAC
     asn ser ser ser arg ala ile his val his gln phe gly asp 430  CTG AGC CAG GGC TGC GAG TCC ACC GGG CCC CAC TAC AAC CCG
     leu ser gln gly cys glu ser thr gly pro his tyr asn pro 472  CTG GCC GTG CCG CAC CCG CAG CAC CCG GGC GAC TTC GGC AAC
     leu ala val pro his pro gln his pro gly asp phe gly asn 514  TTC GCG GTC CGC GAC GGC AGC CTC TGG AGG TAC CGC GCC GGC
     phe ala val arg asp gly ser leu trp arg tyr arg ala gly 556  CTG GCC GCC TCG CTC GCG GGC CCG CAC TCC ATC GTG GGC CGG
     leu ala ala ser leu ala gly pro his ser ile val gly arg 598  GCC GTG GTC GTC CAC GCT GGC GAG GAC GAC CTG GGC CGC GGC
     ala val val val his ala gly glu asp asp leu gly arg gly 640  GGC AAC CAG GCC AGC GTG GAG AAC GGG AAC GCG GGC CGG CGG
     gly asn gln ala ser val glu asn gly asn ala gly arg arg 682  CTG GCC TGC TGC GTG GTG GGC GTG TGC GGG CCC GGG CTC TGG
     leu ala cys cys val val gly val cys gly pro gly leu trp 724  GAG CGC CAG GCG CGG GAG CAC TCA GAG CGC AAG AAG CGG CGG
     glu arg gln ala arg glu his ser glu arg lys lys arg arg 766  CGC GAG AGC GAG TGC AAG GCC GCC TGA GCGCGGCC CCCACCCGGC
     arg glu ser glu cys lys ala ala
```

FIG. 4-1

```
811   GGCGGCCAGG GACCCCCGAG GCCCCCCTCT GCCTTTGAGC TTCTCCTCTG

861   CTCCAACAGA CACCTTCCAC TCTGAGGTCT CACCTTCGCC TCTGCTGAAG

911   TCTCCCCGCA GCCCTCTCCA CCCAGAGGTC TCCCTATACC GAGACCCACC

961   ATCCTTCCAT CCTGAGGACC GCCCCAACCC TCGGAGCCCC CCACTCAGTA

1011  GGTCTGAAGG CCTCCATTTG TACCGAAACA CCCCGCTCAC GCTGACAGCC

1061  TCCTAGGCTC CCTGAGGTAC CTTTCCACCC AGACCCTCCT TCCCCACCCC

1111  ATAAGCCCTG AGACTCCCGC CTTTGACCTG ACGATCTTCC CCCTTCCCGC

1161  CTTCAGGTTC CTCCTAGGCG CTCAGAGGCC GCTCTGGGGG GTTGCCTCGA

1211  GTCCCCCCAC CCCTCCCCAC CCACCACCGC TCCCGCGGCA AGCCAGCCCG

1261  TGCAACGGAA GCCAGGCCAA CTGCCCCGCG TCTTCAGCTG TTTCGCATCC

1311  ACCGCCACCC CACTGAGAGC TGCTCCTTTG GGGGAATGTT TGGCAACCTT

1361  TGTGTTACAG ATTAAAAATT CAGCAATTC    SEQ ID NO: 3
```

FIG. 4-2

Exon 1

5' ATA AAG TAG TCG CGG AGA CGG 3'    SEQ ID NO: 4

5' GCC TTC TGC TCG AAA TTG ATG 3'    SEQ ID NO: 5

Exon 2

5' ACT CTC TCC AAC TTT GCA CTT 3'    SEQ ID NO: 6

5' CCC ACC TGC TGT ATT ATC TCC 3'    SEQ ID NO: 7

Exon 3

5' GAA TGT ATT TGG GAA CTT TAA TTC 3'    SEQ ID NO: 8

5' TAG ATG AGT CAG CAA GTT CAA AAG 3'    SEQ ID NO: 9

Exon 4

5' CAT ATA GGC ATG TTG GAG ACT 3'    SEQ ID NO: 10

5' GAA AGA TAC ATG ACT GTA CTG 3'    SEQ ID NO: 11

Exon 5

5' GTA TTG TTG GGA GGA GGT AGT GAT 3'    SEQ ID NO: 12

5' GCA GGA TAA CAG ATG AGT TAA GGG 3'    SEQ ID NO: 13

FIG. 5

SOD-2

5' GCA ACA TCA AGA AAT GCT AC 3'    SEQ ID NO: 14

5' GGC ACT CGT GGC TGT GGT GGC TTC 3'    SEQ ID NO: 15

SOD-3

5' CAC AAA GGT AGC CAA ACA TTC 3'    SEQ ID NO: 16

5' GTG CAG CTC TCT TTT CAG GAG 3'    SEQ ID NO: 17

FIG. 6

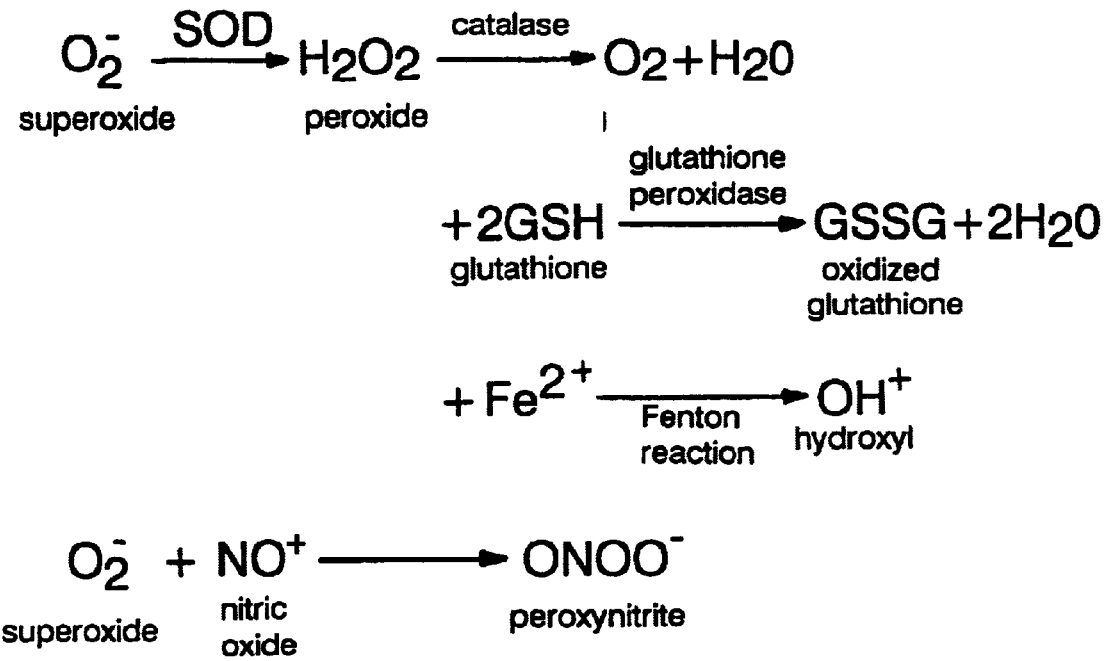

FIG. 7

EXON 1

| FALS | | | | | | | | | V | | | | | | | | | | | | |
|---|---|---|---|---|---|---|---|---|---|---|---|---|---|---|---|---|---|---|---|---|---|
| human | (M) | A | T | - | K | A | V | C | V | L | K | G | D | G | P | V | Q | G | I | I | N F E Q K |
| cow | (M) | A | T | - | K | A | V | C | V | L | K | G | D | G | P | V | Q | G | T | I | H F E A K |
| pig | | A | T | - | K | A | V | C | V | L | K | G | D | G | P | V | Q | G | T | I | Y F E L K |
| mouse | (M) | A | M | - | K | A | V | C | V | L | K | G | D | G | P | V | Q | G | T | I | H F E Q K |
| Xenopus | | | V | - | K | A | V | C | V | L | A | G | S | G | D | V | K | G | V | V | R F E Q Q |
| swordfish | | V | L | - | K | A | V | C | V | L | R | G | A | G | E | T | T | G | T | V | Y F E Q E |
| Drosophila | (M) | V | V | - | K | A | V | C | V | I | N | G | D | A | K | - | - | G | T | V | F F E Q E |
| tomato | (M) | V | - | K | A | V | A | V | L | N | S | S | E | G | V | S | G | T | Y | L | F T Q V |
| spinach | | A | T | K | K | A | V | A | V | L | L | G | T | S | N | V | E | G | V | V | T L T Q E |
| maize | (M) | V | - | K | A | V | A | V | L | A | G | T | - | D | V | K | G | T | I | F | F S Q E |
| Neurospora | (M) | V | - | K | A | V | A | V | V | K | G | D | S | N | V | K | G | T | V | I | F E Q E |
| S. cerevisiae | | | V | - | Q | A | V | A | V | L | K | G | D | A | G | V | S | G | V | V | K F E Q A |

FIG. 8C

Exon 1

EXON 1

127

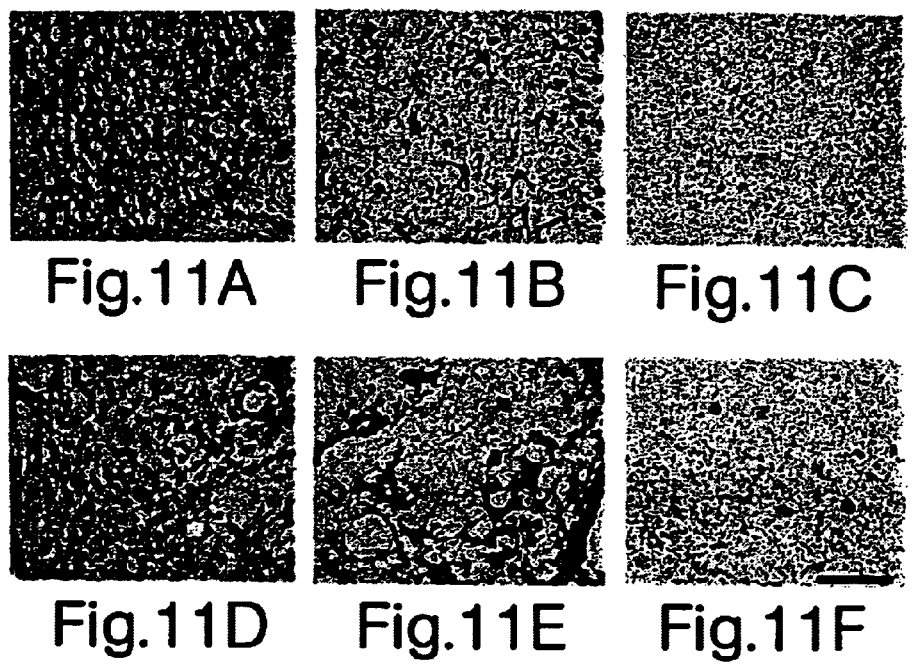
Fig.11A  Fig.11B  Fig.11C
Fig.11D  Fig.11E  Fig.11F
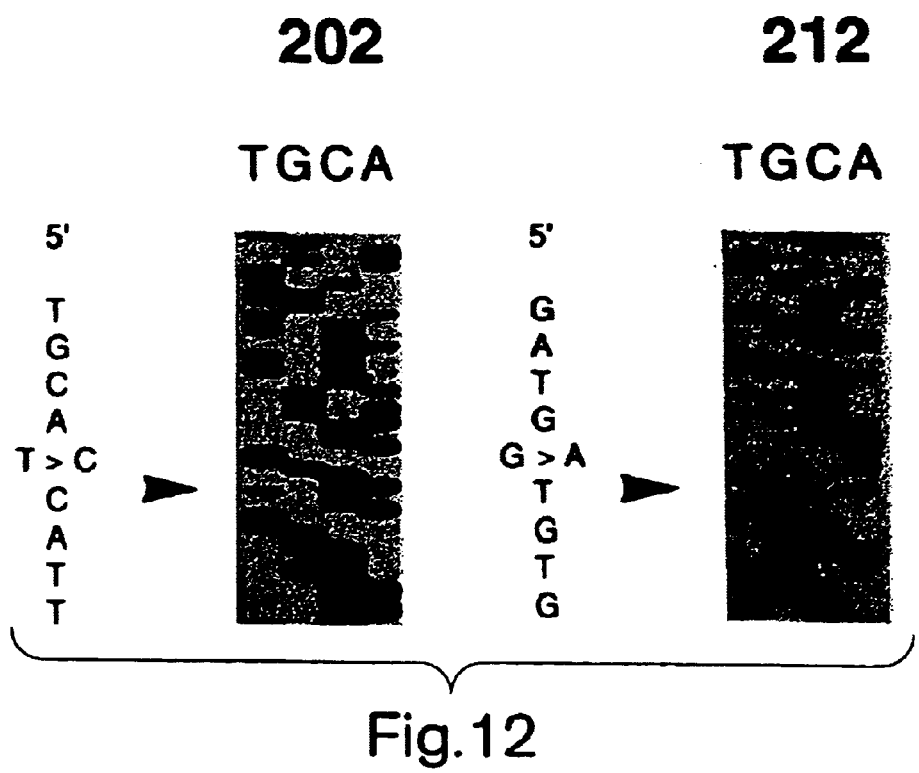
Fig.12

MICE HAVING A MUTANT SOD-1-ENCODING TRANSGENE

CROSS REFERENCE TO RELATED APPLICATIONS

This application is a continuation-in-part of U.S. Ser. No. 08/023,980 filed Feb. 26, 1993.

STATEMENT AS TO FEDERALLY SPONSORED RESEARCH

Funding for the work described herein was provided in part by the Federal government through N.I.N.D.S. Research Grant No. IPOINS31248-01. The Federal government has certain rights in the invention.

BACKROUND OF THE INVENTION

The invention relates to cell death diseases.

Neurodegenerative diseases include familial and sporadic amyotrophic lateral sclerosis (FALS and ALS, respectively), familial and sporadic Parkinson's disease, Huntington's disease, familial and sporadic Alzheimer's disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, Gilles de la Tourette syndrome, and Hallervorden-Spatz disease. Most of the diseases are typified by onset during the middle adult years and lead to rapid degeneration of specific subsets of neurons within the neural system, ultimately resulting in premature death. There is no known cure nor is there an effective therapy to slow the progression for any of the stated diseases.

Amyotrophic lateral sclerosis (ALS) is the most commonly diagnosed progressive motor neuron disease. The disease is characterized by degeneration of motor neurons in the cortex, brainstem and spinal cord (*Principles of Internal Medicine*, 1991 McGraw-Hill, Inc., New York; Tandan et al. *Ann. Neurol*, 18:271–280, 419–431, 1985). Generally, the onset is between the third and sixth decade, typically in the sixth decade. ALS is uniformly fatal, typically within five years (Kurland et al., *Proc Staff Meet Mayo Clin*, 32:449–462, 1957). The cause of the disease is unknown and ALS may only be diagnosed when the patient begins to experience asymmetric limb weakness and fatigue, localized fasciculation in the upper limbs and/or spasticity in the legs which typifies onset.

In ALS the neurons of the cerebral cortex and anterior horns of the spinal cord, together with their homologues in some of the motor nuclei of the brain stem, are affected. The class of neurons affected is highly specific: motor neurons for ocular motility and sphincteric motor neurons of the spinal cord remain unaffected until very late in the disease. Although death occasionally results shortly after the onset of the symptomatic disease, the disease generally ends with respiratory failure secondary to profound generalized and diaphragmatic weakness.

About 10% of ALS cases are inherited as an autosomal dominant trait with high penetrance after the sixth decade (Mulder et al. *Neurology*, 36:511–517, 1986; Horton et al. *Neuroloay*, 26:460–464, 1976). In almost all instances, sporadic and autosomal dominant familial ALS (FALS) are clinically similar (Mulder et al. *Neurology*, 36:511–517, 1986; Swerts et al., *Genet. Hum*, 24:247–255, 1976; Huisquinet et al., *Genet*. 18:109–115, 1980). It has been shown that in some but not all FALS pedigrees the disease is linked to a genetic defect on chromosome 21q (Siddique et al., *New Engl. J. Med.*, 324:1381–1384, 1991.

Parkinson's disease (paralysis agitans) is a common neurodegenerative disorder which appears in mid to late life. Familial and sporadic cases occur, although familial cases account for only 1–2 percent of the observed cases. The neurological changes which cause this disease are somewhat variable and not fully understood. Patients frequently have nerve cell loss with reactive gliosis and Lewy bodies in the substantia nigra and locus coeruleus of the brain stem. Similar changes are observed in the nucleus basalis of Meynert. As a class, the nigrostriatal dopaminergic neurons seem to be most affected.

The disorder generally develops asymmetrically with tremors in one hand or leg and progresses into symmetrical loss of voluntary movement. Eventually, the patient becomes incapacitated by rigidity and tremors. In the advanced stages the disease is frequently accompanied by dementia.

Diagnosis of both familial and sporadic cases of Parkinson's disease can only be made after the onset of the disease. Anticholinergic compounds, propranolol, primidone and levodopa are frequently administered to modify neural transmissions and thereby suppress the symptoms of the disease, though there is no known therapy which halts or slows the underlying progression. Deprenyl has shown some therapeutic promise.

Huntington's disease is a progressive disease which is always transmitted as an autosomal dominant trait. Individuals are asymptomatic until the middle adult years, although some patients show symptoms as early as age 15. Once symptoms appear, the disease is characterized by choreoathetotic movements and progressive dementia until death occurs 15–20 years after the onset of the symptoms.

Patients with Huntington's disease have progressive atrophy of the caudate nucleus and the structures of the basal ganglia. Atrophy of the caudate nucleus and the putamen is seen microscopically where there is an excessive loss of neural tissue. However, there are no morphologically distinctive cytopathological alterations which have been observed.

Although some of the characteristic mental depression and motor symptoms associated with Huntington's may be suppressed using tricyclic antidepressants and dopamine receptor antagonists, respectively, no therapy exists for slowing or preventing of the underlying disease process. Huntington's disease appears to map to a single locus on chromosome 4 and a linkage test currently exists for the clinical assessment of disease risk in presymptomatic individuals with afflicted relatives.

Hallervorden-spatz disease is a neurodegenerative disease which affects the neurons in the region of the basal ganglia. The symptoms generally appear during childhood and adolescence and the disease appears with an inheritance pattern that appears to be autosomal recessive. Patients show abnormalities in muscle tone and movement such a choreoathetosis and dystonia similar to that seen in parkinsonism. As the disease progresses there is increasing dementia. Death generally occurs approximately ten years after onset.

There is no known presymptomatic diagnosis, cure or treatment for Hallervorden-Spatz disease. However, iron toxicity has recently been implicated in the progression of this disease Greenfield, *Neuropathology*, W. Blackwood & J. A. N. Corsellis, Eds. (Edinborgh; T. and A. Constable, Ltd., 1976) pages 178–180. As a result of this implication, the chelating agent deferoxamine mesylate has been administered to patients. However, this therapeutic approach has shown no definite benefit (Harrison's Principles of Internal Medicine, Wilson et al. Eds., McGraw-Hill, Inc., New York, 1991).

Alzheimer's disease is the most important of the neurodegenerative diseases due to the high frequency of occurrence within the population and the fatal course of the disease. Two forms of the disease exist: presenile dementia, in which the symptoms emerge during middle age, and senile dementia which occurs in the elderly. Both forms of the disease appear to have the same pathology. A clear genetic predisposition has been found for presenile dementia. Familial autosomal dominant cases have been reported and the majority of individuals with trisomy 21 (Down's syndrome) develop presenile dementia after the age of 40. The familial Alzheimer's cases map to chromosomes 14, 19 and 21, with more than one locus on 21.

Olivopontocerebellar atrophy (OPCA) is a disease classification which includes a number of disorders characterized by a combination of cerebellar cortical degeneration, atrophy of the inferior olivary nuclei and degeneration and disappearance of the pontine nuclei in the basis pontis and middle cerebellar peduncles. Autosomal dominant inheritance is characteristic in most families. In one family, termed the Schut family, genetic linkage has been shown to chromosome 6. An excess of glutamate has been implicated as the causative agent in this disease. A gene with an expanded CAG trinucleotide repeat [causes one form of OCPA] ha snow been identified and eluted sequencing can be used for diagnosis (Orr et al., *Nature Genetics* 4:221–226, 1993).

The human superoxide dismutases are actually at least three different enzymes: cytosolic Cu/Zn superoxide dismutase encoded by the SOD1 gene on chromosome 21 (Levanon et al., *EMBO J.* 77–84, 1985 and Hjalmarsson et al., *P.N.A.S.* 84:6340–6344, 1987); mitochondrial superoxide dismutase encoded by the SOD2 gene on chromosome 6 (Wispe et al., *Biochim. Biophys. Acta.* 994:30–36, 1989); and extracellular superoxide dismutase encoded by the SOD3 gene on chromosome 4 (Hjalmarsson, supra). SOD1, for example, is a homodimeric metalloenzyme that catalyzes the dismutation of the toxic superoxide anion $O_2-$ to $O_2$ and $H_2O_2$. The major function of the superoxide dismutase is to eliminate $O_2-$ resulting from aerobic respiration. As a class of polypeptides present in most living organisms, these enzymes are differentially associated with different metals including iron, manganese, copper and copper-zinc.

In Guam an inherited disease termed Parkinsonism-dementia complex has been described. Clinical, pathological and familial studies have indicated that this disease is a clinical variant of the local form of ALS. Cases of presenile dementia in the absence of ALS or Parkinsonism have also been observed in this population (Kurland et al. In Norris FH Jr. and Kurland LT eds. *Motor Neuron Diseases: Research on amyotrophic lateral sclerosis and related disorders*. NY: Grune & Stratton, 1969; 84:28–50; Hirano et al., Brain 84:642–661, 1961; and Hirano et al., Brain 84:662–679, 1961).

Hallewell et al. (U.S. Pat. No. 5,066,591) describe methods and compositions for the production of human copper/zinc superoxide dismutase polypeptides in microorganisms.

Hallewell (U.S. Pat. No. 5,084,390) describe recombinant Cu/Zn superoxide dismutase polymers having an extended in vivo half-life composed of SOD monomers covalently coupled to each other.

Bruice (International Patent Application No. PCT/US91/06558) describe synthetic enzymes that mimic catalytic activity of superoxide dismutase.

Bracco et al. (P.S.E.B.M. 196:36–41, 1991) have measured the levels of superoxide dismutase in the cerebral spinal fluid of patients with age-related neurodegenerative disorders including ALS, Alzheimer's disease, and a reference group of normal subjects. Bracco et al. report that the superoxide dismutase activity was found to increase with the age of the subject while no significant correlation was found in the ALS and Alzheimer's disease patients. The activity mean values were found to be significantly lower in patients with ALS and Alzheimer's disease.

Liu et al. (Amer. Physiol. Soc. H589-H593, 1989) describe the administration of polyethylene glycol-conjugated superoxide dismutase and catalase to reduce ischemic brain injury in rats.

Olanow (Ann Neurol. 32:52–59, 1992) have proposed free radicals as the cause of neuronal injury in several neurological disorders, including Parkinson's disease and ischemic brain injury.

SUMMARY OF THE INVENTION

We have discovered that mutations in superoxide dismutase cause familial amylotrophic lateral sclerosis. Accordingly we have determined methods for the diagnosis and treatment of amyotrophic lateral sclerosis and other cell death disease, particularly neurodegenerative diseases. Methods are provided for treating familial amyotrophic lateral sclerosis and amyotrophic lateral sclerosis as well as other cell death diseases which are the result of decreased SOD activity, altered SOD enzymatic activity, and altered SOD physical characteristics. In addition, therapeutics for diseases caused by alterations in the SOD biochemical pathway are provided.

In the first aspect, the invention features methods of diagnosing an increased likelihood of developing cell death disease in a patient. The methods include analyzing the DNA of the patient to determine whether the DNA contains a mutation in SOD coding sequence, such a mutation being an indication that the patient has an increased likelihood of developing a cell death disease. The methods may be used to diagnose a cell death disease, particularly neurodegenerative disease, more particularly Parkinson's disease, Huntington's disease, Alzheimer's disease, Hallervorden-Spatz disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, Gilles de la Tourette syndrome, and Hallervorden-Spatz disease, and ALS which is familial, sporadic typical, or atypical in nature. These methods may also be used for the diagnosis of a SOD related disease in a fetus.

The methods may include amplifying a SOD-encoding gene of the patient using SOD-specific primers, and then analyzing the amplified gene. The DNA may be analyzed by nucleotide sequencing, SSCP analysis, RFMP, heteroduplex analysis or RFLP analysis. The amplifying may be carried out by PCR reaction, by reverse transcriptase PCR or by any other method available to obtain a sufficient amount of DNA.

The primer sequence may be derived from SOD1 nucleic acids, SOD2 nucleic acids, SOD3 nucleic acids or nucleic acids from any other human SOD gene.

Antibodies which recognize familial amyotrophic lateral sclerosis SOD polypeptides but fail to recognize wild-type SOD may also be used for the diagnosis of familial amyotrophic lateral sclerosis in patients.

In the second aspect, the invention features kits for the diagnosis of a cell death disease in a patient. The kits may include one or more SOD gene-specific PCR primers or antibodies recognizing the SOD polypeptides. The PCR primers may include a SOD1-specific nucleic acid sequences, SOD2-specific nucleic acid sequences, SOD3-specific nucleic acid sequences. These kits may be used to diagnose any of the above-referenced diseases.

Kits which include antibodies which specifically recognize mutant SOD polypeptides present in amyotrophic lateral sclerosis patients are part of the kits of the inventor.

In the third aspect, the invention features methods of treating a patient with a disease involving a mutant SOD encoding gene or environmentally induced ALS. The methods include administering to the patient an antioxidant, effective to reduce the symptoms the disease in the patient. The antioxidant may be vitamin C, vitamin E, a lazaroid, BHA, BHT, Beta-carotene, urate, bilirubin, glutathione, dimercaptrol lutein, upiguinol-10, dithiothreotol, mercaptan, a sulfa compound, methionine, cystein, or N-acetyl cysteine, or any other antioxidant which reduces the level of toxic compounds in the affected cells. Most preferably, the antioxidant is vitamin C or vitamin E.

Also included are methods of treating a patient with a disease involving a mutant SOD encoding gene or a patient with sporadic ALS due to environmental causes which include administering to the patient SOD polypeptide, in an amount effective to reduce the symptoms of said disease in said patient. The SOD polypeptide may be SOD Cu/ZnSOD, mSOD, ecSOD, or derivatives, as described below.

Methods of treating the above patients may also include administering to the patient a chelating agent, e.g. desferoxamine, or transgene including a nucleotide sequence encoding a SOD polypeptide e.g., a nucleotide sequence which encodes the Cu/ZnSOD polypeptide, the mSOD polypeptide, or ecSOD polypeptide. Preferably, the nucleotide sequence encodes Cu/ZnSOD or mSOD, and most preferably the nucleotide sequence encodes Cu/ZnSOD.

Also included in the invention is a method for treating a patient with a disease involving a mutant SOD encoding gene. This method includes first identifying a mutant SOD polypeptide-encoding gene in the DNA of the patient, and, second, administering to the patient a therapeutic amount of the anti-sense RNA homolog of a gene encoding a SOD polypeptide. The polypeptide may be wild-type SOD or a polypeptide encoded by the mutant SOD-encoding gene.

Also included is a method for treating a patient with a disease involving a mutant SOD encoding gene, wherein the mutant SOD polypeptide-encoding gene in the DNA is identified in the patient, and a therapeutic amount of a transgene encoding the wild-type homolog of the mutant SOD polypeptide is administered.

Further included is a method for treating a patient with a disease involving a mutant SOD-encoding gene, which comprises identifying the mutant SOD polypeptide-encoding gene in the DNA of the patient, and administering to the patient a therapeutic amount of a transgene encoding the anti-sense homolog of said wild-type SOD RNA.

Also a part of the invention is a method of treating a patient with a disease involving a mutant SOD encoding gene by administering to the patient an antibody which is sufficient to partially inactivate said mutant SOD polypeptide.

A method of treating a patient with a disease involving a mutant SOD encoding gene or a patient with sporadic ALS due to environmental causes either of whose disease is caused at least in part by excess SOD activity by administering to the patient an inhibitor of wild-type SOD, such as those provided herein, is a part of the invention.

A method of treating a patient with a disease involving a deleterious mutant SOD encoding gene or a patient with sporadic ALS due to environmental causes by the administering of a mutant SOD polypeptide with increased SOD enzymatic activity compared to wild-type SOD is also included as a part of the invention. Such a patient may also be treated by administering a nucleotide sequence encoding a non-wild-type therapeutic SOD polypeptide mutant different from and capable of inhibiting the deleterious SOD polypeptide. As in all methods, this SOD polypeptide may be a fragment of SOD, an analog of SOD, or a non-peptide mimetic of SOD.

Further included is a method of treating a patient with a disease involving a mutant SOD encoding gene by administering to the patient a compound which participates in a biochemical pathway involving a SOD polypeptide. These compounds may include glutathione peroxidase, catalase, or nitric oxide synthase. Specifically, peroxide-reducing polypeptides may be administered, as described below.

The invention also includes methods of treating or preventing ALS and FALS by the administration of inhibitors and agonists of SOD. This method is appropriate in patients in whom SOD gene which encodes a polypeptide which confers altered or increased SOD enzymatic activity. The chelating agent may be disferoxamine, EDTA, EGTA, DETC, BCDA, penicillamine, tetracycline, a metallothionein protein or an apo-metal binding protein. The metallothionein protein may be a yeast copper metallotheonein. The apo-metal binding protein may be one or more of apo-superoxide dismutase, hemoglobin, myoglobin, or plastocyanin.

Any of the methods described herein may be used alone or in combination. For example, it may be desirable to administer one or more antioxidants in combination with a chelating agent and or a SOD polypeptide therapeutic.

Any of the following diseases may be treated using one or more of the above methods: a cell death disease, particularly a neurodegenerative disease, more particularly Parkinson's disease, Huntington's disease, Alzheimer's disease, Hallervorden-Spatz disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, Gilles de la Tourette syndrome, and ALS which is familial, sporadic typical, or atypical in nature.

In a fourth aspect, the invention features antibodies reactive with a FALS polypeptide but not significantly reactive with a wild-type SOD polypeptide. These antibodies may be monoclonal or polyclonal and may be obtained by subtractive techniques. The antibodies may be sufficient for the inactivation of a SOD polypeptide.

These antibodies may be used as stated above to diagnose ALS in a patient by contacting a blood sample of said patient with the antibody.

In a fifth aspect, the invention features methods of treating a patient with a neoplasm by administering to the patient a FALS polypeptide. A patient with a neoplasm, may also be treated by the administration of transgene encoding an FALS polypeptide.

In the sixth aspect, the invention features a transgenic non-human animal whose somatic and germ cells contain a transgene for a disease-causing mutant SOD polypeptide having a nucleic acid sequence encoding a disease causing SOD polypeptide in an expressible genetic construction. The animal may be a mouse, a worm, or any other animal useful for research or drug development.

In the seventh aspect, the invention features a bacterial or yeast cell containing purified nucleic acid derived from a FALS gene.

The eighth aspect, the invention features purified DNA encoding a purified FALS polypeptide, purified RNA encoding a purified FALS polypeptide, and purified FALS polypeptide.

A ninth aspect of the invention is the use of any of the methods or compounds of the invention which do not solely depend upon the physical properties of a mutant SOD polypeptide for the treatment of a disease of cell death which is the result of a mutation or imbalance in a component of the SOD pathway other than the SOD polypeptide. For example, treatment of diseases due to defects in the production or function of glutathione peroxidase, catalase and nitric oxide synthase. Methods useful for the treatment of these disorders include administration of wild-type and mutant SOD, anti-sense RNA to SOD encoding sequences, use of antibodies to wild-type SOD, and use of analogs and inhibitors of compounds in the SOD pathway.

More specifically, the invention provides therapies using Cu/Zn superoxide dismutase (Cu/ZnSOD), mitochondrial superoxide dismutase (mSOD), or extracellular superoxide dismutase (ecSOD) (FIGS. 2–4 and SEQ ID NOS: 1–3, respectively), as well as other naturally occurring superoxide dismutase polypeptides. Also included are: allelic variations; natural mutants; induced mutants; proteins encoded by DNA that hybridizes under high (e.g., washing at 2xSSC at 40 C with a probe length of at least 40 nucleotides) stringency conditions to naturally occurring Cu/Zn SOD, mSOD, or ecSOD-encoding nucleotide sequences, i.e. SOD1, SOD2, or SOD3; for other definitions of high and low stringency see Current Protocols in Molecular Biology, John Wiley & Sons, New York, 1989, 6.3.1–6.3.6, hereby incorporated by reference). The term "SOD polypeptide" also includes chimeric polypeptides that include Cu/ZnSOD, mSOD, or ecSOD together with unrelated sequences.

The invention also includes any biologically active fragment or analog of Cu/ZnSOD, mSOD or ecSOD. By "biologically active" is meant possessing therapeutically useful superoxide reducing activity which is characteristic of the Cu/ZnSOD, mSOD, or ecSOD polypeptides shown in FIGS. 2–4 (SEQ ID NOS: 1–3). Therapeutically useful activity of a Cu/ZnSOD, mSOD or ecSOD fragment or Cu/ZnSOD, mSOD, or ecSOD analog, can be determined in any of a variety of Cu/ZnSOD, mSOD or ecSOD assays. For example, those assays described in Wayne and Fridovich (Analytical Biochemistry, 161: 559–566 (1987)), McCord and Fridovich (*J. of Biol. Chem.*, 244: 6049–6055 (1969)), and Salin and McCord (*J. of Clin. Invest.*, 54:1005–1009 (1974)) may be used to determine superoxide dismutase activities of Cu/ZnSOD, mSOD or ecSOD. A Cu/ZnSOD, mSOD or ecSOD analog possessing, most preferably 90%, preferably 40%, or at least 10% of the activity of a wild-type or mutant Cu/Zn SOD, mSOD, or ecSOD polypeptide (shown in FIGS. 2–4; SEQ ID NOS: 1–3), in any in vivo or in vitro Cu/ZnSOD, mSOD or ecSOD assay (e.g., those described herein) is considered biologically active and useful in the methods of the invention.

Preferred analogs include 155-amino acid Cu/Zn SOD, 222 amino acid mSOD, or 240 amino acid ecSOD (or biologically active fragments thereof) whose sequences differ from the wild-type sequence only by conservative amino acid substitutions, for example, substitution of one amino acid for another of the same class (e.g., valine for glycine, arginine for lysine, etc.) or by one or more non-conservative amino acid substitutions, deletions, or insertions which do not destroy the polypeptide's relevant biological activity as measured using in vivo or in vitro (e.g., those described above). Preferred analogs also include Cu/ZnSOD, mSOD, or ecSOD (or biologically active fragments thereof) which are modified for the purpose of increasing peptide stability; such analogs may contain, for example, one or more desaturated peptide bonds or D-amino acids in the peptide sequence.

Analogs can differ from naturally occurring Cu/ZnSOD, mSOD, or ecSOD polypeptides by amino acid sequence differences or by modifications that do not involve sequence, or by both. Analogs useful for the methods of the invention will generally exhibit at least 65%, more preferably 80%, even more preferably 90%, and most preferably 95% or even 99%, homology with all or part of a naturally occurring Cu/ZnSOD, mSOD, or ecSOD sequence. The length of comparison sequences will generally be at least about 15 amino acid residues, preferably more than 40 amino acid residues. Modifications include in vivo, or in vitro chemical derivatization of polypeptides, e.g., acetylation, glycosylation, or carboxylation. Also embraced are versions of the same primary amino acid sequence that have phosphorylated amino acid residues, e.g., phosphotyrosine, phosphoserine, or phosphothreonine. Analogs can differ from naturally occurring Cu/ZnSOD, mSOD, or ecSOD polypeptides by alterations of their primary sequence. These include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

The invention also provides methods of using SOD polypeptides (or nucleotide sequences encoding polypeptides) which are obtained from other living organisms which are found to synthesize superoxide dismutases, e.g., *E.coli, Saccharomyces cerevisiae*, and *C. elegans*. Useful mutants of such SOD polypeptides are those which have increased stability or other desirable properties.

The invention also includes therapeutic uses of polypeptides (or nucleotide sequences encoding polypeptides) which are substantially (at least 70%) homologous to wild-type SOD polypeptides or genes. "Homologous" refers to the sequence similarity between two polypeptides or nucleic acids. When a position in both of the two compared sequences is occupied by the same base or amino acid monomeric subunit, e.g., if a position in each of the two DNA molecules is occupied by adenine, then the molecules are homologous at that position. The homology between two sequences is a function of the number of matching or homologous positions shared by the two sequences. For example, if 6 of 10 of the positions in two sequences are homologous, then the two sequences are 60% homologous. By way of example, the DNA sequences ATTGCC and TATGGC are 50% omologous.

The invention also includes uses of the compounds described herein in the manufacture of medicaments to be used in the diagnosis and treatment of patients with any of the cell death diseases.

Substantially pure Cu/ZnSOD, mSOD, and ecSOD polypeptides can be produced in quantity using standard recombinant DNA-based techniques. Thus, recombinant Cu/ZnSOD, mSOD2, or ecSOD polypeptides can be administered with a pharmaceutically acceptable diluent, carrier, or excipient, in unit dosage form.

Conventional pharmaceutical practice may be employed to provide suitable formulations or compositions to administer the polypeptide to patients suffering from or presymptomatic for a disease of cell death.

Further included as an aspect gene of the invention are the FALS-SOD polypeptides, e.g., those polypeptides encoded by the nucleic acid of patients with FALS due to a SOD mutation. Also included are the nucleic acids which encode these mutant polypeptides. Also included as an aspect of the invention are antibodies, particularly monoclonal antibodies, which are reactive with FALS-SOD polypeptides.

In addition to substantially full-length polypeptides, the invention also includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of Cu/ZnSOD, MSOD, or ecSOD can be generated by methods known to those skilled in the art. The ability of a candidate fragment to exhibit a biological activity of Cu/ZnSOD, mSOD, or ecSOD can be assessed by methods described below. Also included are Cu/ZnSOD, mSOD, or ecSOD polypeptides containing amino acids that are normally removed during protein processing (for example, the leader sequence of ecSOD), including additional amino acids that are not required for the biological activity of the polypeptide, or including additional amino acids (if any) that result from alternative mRNA splicing or alternative protein processing events.

The invention also provides methods of using SOD polypeptides (or nucleotide sequences encoding polypeptides) which are obtained from other living organisms which are found to synthesize superoxide dismutases, e.g., *E.coli, Saccharomyces cerevisiae,* and *C. elegans.* Useful mutants of such SOD polypeptides are those which have increased stability or other desirable properties.

The invention also includes therapeutic uses of polypeptides (or nucleotide sequences encoding polypeptides) which are substantially (at least 70%) homologous to wild-type SOD polypeptides or genes. "Homologous" refers to the sequence similarity between two polypeptides or nucleic acids. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions share by the two sequences. For example, if 6 of 10 of the positions in two sequences are homologous, then the two sequences are 60% homologous. By way of example, the DNA sequences ATTGCC and TATGGC are 50% homologous.

Substantially pure Cu/ZnSOD, mSOD, and ecSOD polypeptides can be produced in quantity using standard recombinant DNA-based techniques. Thus, recombinant Cu/ZnSOD, mSOD2, or ecSOD polypeptides can be administered with a pharmaceutically acceptable diluent, carrier, or excipient, in unit dosage form.

Conventional pharmaceutical practice may be employed to provide suitable formulations or compositions to administer the polypeptide to patients suffering from or presymptomatic for a disease of cell death. A "substantially pure" preparation of a polypeptide is a preparation which is substantially free (e.g., to the extent required for formulating Cu/ZnSOD, mSOD2, or ecSOD into a therapeutic composition) of the proteins with which it naturally occurs in a cell.

The formulations of the invention can be administered for example, by parenteral, intravenous, subcutaneous, intramuscular, intracranial, intraorbital, ophthalmic, intraventricular, intracapsular, intraspinal, intracisternal, intraperitoneal, ihtranasal, aerosol, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain excipients sterile water or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of present factors. Other potentially useful parenteral delivery systems for the factors include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

Toxic SOD mutants and nucleotide sequences encoding such polypeptides can be formulated by any of the above methods for use as therapies for diseases of cell proliferation, e.g., cancer.

Other features and advantages of the invention will be apparent from the following detailed description, and from the claims.

DETAILED DESCRIPTION

The drawings will first be briefly described.

DRAWINGS

FIGS. 1A–1 through 1C–2 are a set of diagrams illustrating the single-strand conformational polymorphism and sequence analysis of SOD1 exons from FALS-affected individuals.

FIGS. 1A–1 and 1A–2 are autoradiograms is an autoradiogram of single strand conformational polymorphism banding patterns for SOD-1 exons 2(top; FIG. 1A–1) and 4(bottom; FIG. 1A–2). "N" designates DNA from normal individuals.

FIGS. 1C–1 and 1C–2 are a comparison of amino acid sequences from exons 1 and 4 of normal Cu/Zn SOD1 obtained from diverse species, as noted.

FIGS. 2–1 through 2–3 are the genomic sequence of SOD1 and Cu/ZnSOD polypeptide (SEQ ID No. 1).

FIGS. 3–1 and 3–2 are the cDNA sequence of SOD2 and mSOD polypeptide (SEQ ID No. 2).

FIGS. 4–1 and 4–2 are the cDNA sequence of SOD3 and the ecSOD polypeptide (SEQ ID No. 3).

FIG. 5 is a list of primers useful for the diagnosis of diseases linked to the SOD1 nucleic acid sequences.

FIG. 6 is a list of primers for reverse transcriptase PCR for the detection and diagnosis of SOD2 and SOD3 linked diseases.

FIG. 7 is a diagram of the pathways for the SOD superoxide dismutase enzymes.

Figure 8A:

FIG. 8A shows single-strand conformational polymorphisms for exon 1 SOD1 DNA amplified from a normal individual (lane N) and a patient with FALS carrying an exon 1 mutation (lane 127).

Figure 8B:

FIG. 8B is sequence analysis from amplified DNA from patient in family 127 with exon 1 mutation. The mutation changes a C to a T in one allele; thus, the patient is heterozygous and has both a C and a T in this double-strand sequence at that base pair (arrow).

FIG. 8C is multi-species comparison of SOD1 protein sequences corresponding to exon 1. The exon 1 mutation substitutes a valine for an alanine that is completely conserved in all of the indicated species. Sources of sequences were human (Levanon et al. (1985) *EMBO J.*, 4, 77–84), bovine (Hallewell et al. (1991) *Biochem. Biophys. Res. Commun.* 181, 474–480), mouse (Benedetto et al. (1991) *Gene* 99, 191–195), *Xenopus* (Montesano et al. (1989) *Eur. J. Biochem.* 186, 421–426), *Drosophila* (Seto et al. (1989) *Gene* 75, 85–92), tomato (Perl-Treves et al. (1988) *Plant Mol. Biol.* 11, 609–623), maize (Cannon et al. (1987) *Isozymes Curr. Top. Biol. Med. Res.* 14, 73–81), *Neurospora* (Chary et al. (1990) *J. Biol. Chem.* 265, 18961–18967), and others (Hjalmarsson et al. (1987) *Proc. Natl. Acad. Sci. USA* 84, 6340–6344).

Figure 9A:
Figure 9B:

FIGS. 9A and 9B are In situ hybridization of 51-mer from coding sequence of human SOD1 to anterior gray matter of normal human lumbosacral spinal cord. Both in FIG. 9A dark and FIG. 9B bright field, there is strong hybridization of probe to large motor neurons.

Figure 10A:
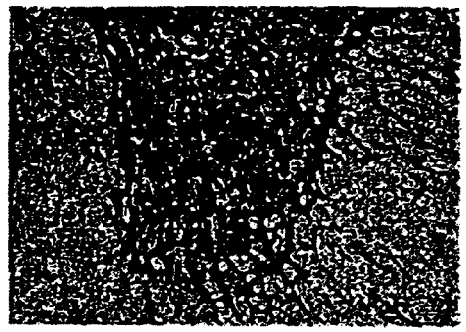
Figure 10B:
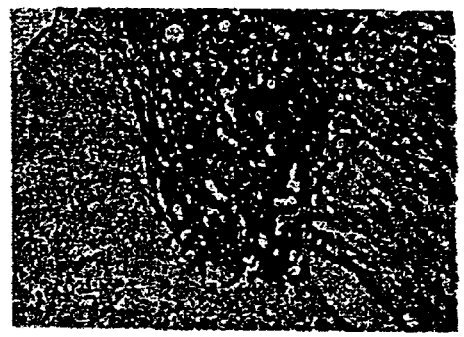
Figure 10C:
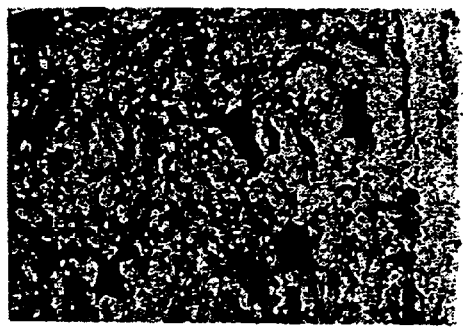
Figure 10D:
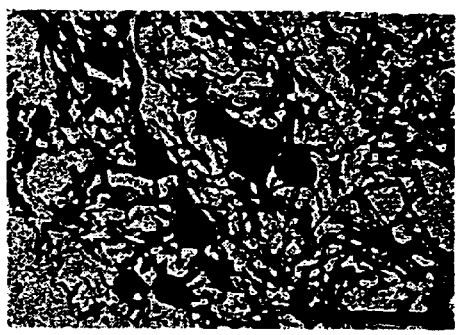

FIGS. 10A through 10D are immunostainings of normal human lumbosacral spinal cord with monoclonal antibodies to SOD1 (FIGS. 10A and 10C) and neurofilament heavy chain (FIGS. 10B and 10D). At low power, the anterior horn shows numerous, heavily staining SOD1-positive cells which at high power have the dimensions and morphology of anterior horn cells. Another section reveals prominent neurofilament staining in this population of neurons, again with the morphology of motor neurons.

FIGS. 11A through 11F are immunostainings of lumbosacral spinal cord from a patient with an exon 1 mutation in SOD1 using monoclonal antibodies to SOD1 (FIGS. 11AA and 11D) and neurofilament (FIGS. 11B and 11E) as well as cresyl violet staining (FIGS. 11C and 11F). The tissue illustrated is from anterior horn (FIGS. 11A, 11B and 11C) and intermediolateral gray matter including Clarke's column (FIGS. 11D, 11E and 11F). In this cord, motor neurons were severely involved at death, as indicated by reduced numbers of this cell type (FIGS. 11B and 11C) compared to normal spinal cord. Little SOD1 staining is evident in the anterior gray matter; there may be one residual, pyknotic motor neuron with some anti-SOD1 reactivity (FIG. 11A, upper left). In contrast, numerous neurons in Clarke's column are evident by immunostaining with SOD1 (FIG. D) and neurofilament (FIG. 11E) as well as by cresyl violet staining (FIG. 11F).

FIG. 12 is an illustration of the single-strand conformation polymorphism and sequence analysis of exon 4.

Figure 13:
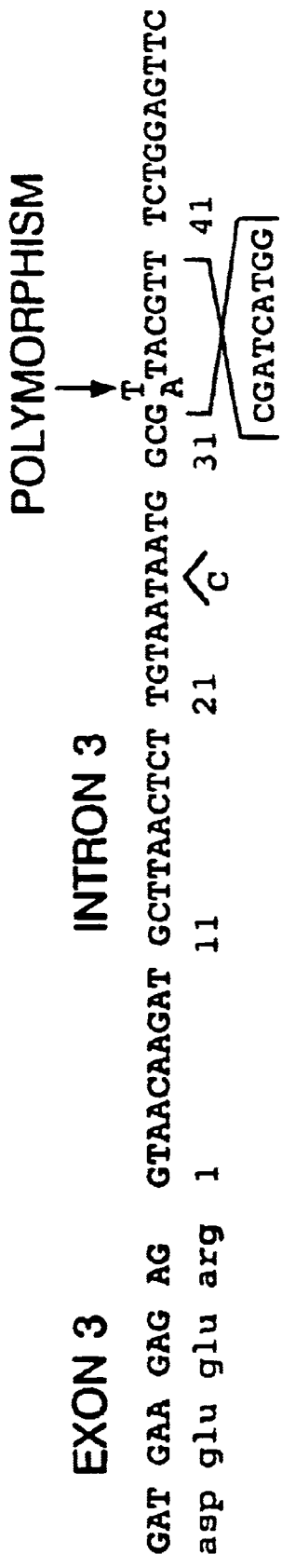

FIG. 13 is an illustration of polymorphism in intron 2 of SOD.

I. IDENTIFICATION OF A CLASS OF GENETIC DEFECTS CAUSING CELL DEATH

Our work has shown that the SOD1 gene is specifically altered in individuals with familial ALS; based on this work, we believe that physical or enzymatic alterations in the mutant SOD polypeptides plays a fundamental role in the etiology of diseases of cell death, particularly neurodegenerative diseases such as ALS.

It is a striking fact that a majority of neurodegenerative diseases, ranging from Alzheimer's disease to Parkinson's disease, have a similar profile for onset and progression. These observations support the thesis that a similar mechanism forms the underlying basis of all of these diseases. Our discovery that abnormal SOD is a causative agent in diseases of cell death provides a heretofore missing disease mechanism.

II. PATHOGENESIS OF ABNERMAL SOD1

FIG. 1C is a comparison of amino acid sequences encoded by exons 2 and 4 of Cu/ZnSOD of several disparate organisms: (human [Levanon et al., *EMBO, J.* 77–84, 1985; Hjalmarsson et al., *Proc. Natl. Acad. Sci.*, 84:6340–6344, 1987]; mouse [Bewley, *Nucl. Acids Res.* 16:2728, 1988]; *Onchocerca volvulus* [Henkle et al., *Infect. Immun.* 59:2063–2069, 1991]; tomato [Perl-Treves et al., *Plant Molec. Biol.* 11:609–623, 1988]; *Saccharomyces cerevisiae* [Bermingham-McDonogh et al.; *Proc. Natl. Acad. Sci. USA* 85:4789–4793, 1988], all others [Hjalmarsson et al., *Proc. Natl. Acad. Sci.* 84:6340–6344, 1987]). The aberrant FALS residues we discovered are denoted at the top of FIG. 1C; their corresponding positions in the coding sequence are indicated at the bottom of the Figure.

We believe that in addition to causing a decrease in the level of cellular protection against oxygen free radicals, the FALS-associated mutations in SOD1 may confer novel properties on the corresponding mutant polypeptides. These novel properties would account for the dominant nature of the disease. Specifically, we believe that mutations in FALS SOD polypeptides confer novel chemical properties to the polypeptides so as to make them directly toxic, e.g., by destabilizing the folding of the polypeptide and causing it to adopt unstable (e.g., susceptible to proteolysis) or insoluble conformations. The mutant polypeptides may, for example, cause disease by impeding the peptide degradation systems of the cell, creating phenotypes, for example peptides which have a toxic biological function failing to efficiently sequester the copper or zinc which are toxic in elevated concentrations actively sequestering metals such as aluminum or cadmium, or by any other mechanism whereby the novel physical or chemical properties of the ALS-SOD polypeptide ultimately kills the cell. It is possible that two or more of these processes may act in a concerted fashion; they are not mutually exclusive. An example of a disease and a gene with mutations that confer such novel chemical properties on the corresponding mutant polypeptide is retinitis pigmentosa and rhodopsin (Sung et al., *PNAS U.S.A.* 88:6481–6485, 1991).

Additionally, the FALS-associated mutations in SOD1 may confer novel enzymatic properties to the corresponding mutant polypeptides, such as catalyzing the synthesis of novel compounds or the synthesis of unusual quantities of compounds which are normally benign. Either phenomenon may occur by interaction of mutant SOD with atypical substrates, such as nitric oxide. The newly created compounds could be directly toxic, such as free radical compounds or agonists/competitors of other enzymes, could be reactive intermediates that lead to formation of toxic compounds, or could be toxic due to the synthesis of an elevated quantity.

This enzymatic toxicity may act alone or in concert with chemical toxicity to kill the cell.

Furthermore, the mutations in ALS-SOD polypeptides are likely to interfere with the normal SOD function of eliminating certain oxygen free radicals (e.g., superoxide) from the cellular environment. A survey of a sample derived from individuals with a variety of different mutations in SOD indicates that there is a loss of in most cases 10%, in some cases 25%, and only rarely more than 50% superoxide free radical elimination from the cell. This loss in free radical scavenging activity may contribute, wholly or in part, to the observed cellular toxicity in ALS. The reduction in oxygen free radical scavenging ability of the mutant SOD polypeptides can act in concert with the chemical and/or enzymatic toxicity of the mutant SOD polypeptides to kill the cell. In any potential treatment for the mitigation or cure of ALS, it is desirable to restore the oxygen free radical scavenging ability of the cell, either by supplementation with functional SOD polypeptide to normal or supranormal levels, or by use of compounds (such as antioxidants) capable of elimination of free radicals. The therapeutic restoration of free radical scavenging in the cell is desirable alone or in combination with other therapies for treatment of ALS.

Another possibility is that the mutations in SOD1 decrease or eliminate SOD1 activity. However, most loss-of-function mutations cause a recessive rather than a dominant effect (Muller In *Proceedings of the Sixth International Congress of Genetics*, pp 213–255, 1932; Park et al., *Genetics* 113:821–852, 1986). Exceptions can arise in proliferating cells that allow a somatic mutation to cause a loss of function of the second allele of the gene, as in the case of retinoblastoma (Dryja et al., *Nature* 339:556–558, 1989).

An additional hypothesis is that the putative FALS mutations have a dominant-negative effect (Herskowitz, *Nature* 219–222, 1987) such that the mutant SOD1 protein not only is functionally defective but also inhibits the function the normal SOD1 protein expressed from the normal allele. Consistent with the increased activity hypothesis, both Ile-113 and Leu-106 residues are thought to be involved in forming hydrogen bonds important for the increased thermostability of a mutant form of SOD1 (Parge et al., *Proc. Natl. Acad. Sci. USA* 89:6109–6113, 1992); it is plausible that SOD1 proteins with amino acid changes at these residues are of increased stability and hence of increased activity. Consistent with the dominant-negative hypothesis, one of the sites abnormal in FALS patients, Ile-113, has been implicated in hydrogen bond formation between SOD1 monomers (Kitagawa et al., *J. Biochem* 109:477–485, 1991); the normal and mutant proteins may combine to form an inactive heterodimer.

III. DIAGNOSTICS FOR NEURODEGENERATIVE DISORDERS

Neurodegenerative disorders may be diagnosed in a patient using the primers provided in FIG. 5 for the SOD1 gene and in FIG. 6 for the SOD2 and SOD3 genes. These primers, or other primers derived from the SOD genes, may be used to identify SOD mutations. For example, diagnosis of individuals with neurodegenerative diseases resulting from mutations in the SOD1 gene may be performed using the techniques provided in the examples, below. Mutations in SOD2 and SOD3 may be diagnosed using the primers which are provided (or any primers which are derived from the SOD2 or SOD3 genes) in combination with the technique of reverse transcriptase PCR (Kawasaki and Wang, *PCR Technology* Ehrlich, Ed. (New York, Stockton Press, 1989) pages 89–98. Following amplification of the target DNA, SSCP and/or sequence analysis may be performed. It is desirable to compare the sequenced mutation to the equivalent sequences from affected and unaffected relatives in the case of familial diseases. In cases which do not appear to be familial, the mutation is compared to mutations previously observed in the affected population. Correlation with affected relatives, the diseased population, and residues which are conserved through evolution provide an additional measure of certainty useful for a definitive diagnosis.

Neurodegenerative diseases may also be diagnosed using restriction fragment length polymorphisms or any other diagnostic technique involving the detection of nucleotide changes in the SOD genes, e.g., RFMP, and heteroduplex analysis. Knowing the sequences of the SOD genes, one skilled in the art may design combinations of DNA probes and restriction enzymes to determine the afflicted individuals in a FALS (or other inherited SOD disease) family. See also the example, below.

IV. THERAPIES FOR DISEASES INVOLVING A MUTANT SOD ENCODING GENE

On the basis of our findings, we conclude that toxicity caused by oxygen free radicals is a primary pathogenetic mechanism for motor neuron death in FALS and sporadic ALS. Therapeutic measures that diminish this toxicity will blunt the devastating course of these diseases. These therapeutic approaches are also appropriate for the treatment of presymptomatic individuals with defined SOD mutations as well as symptomatic individuals.

A dominant inheritance pattern is seen in all FALS pedigrees. A dominant phenotype may be conferred by the gain of a novel function by the mutant SOD polypeptide. This gain of function may include alterations of the physical properties, chemical properties, or the enzymatic properties of the mutant SOD polypeptide. For example, dominant negative effects in which the mutant SOD polypeptides inactivate wild type SOD polypeptides by causing loss of activity or stability of a multimeric complex (such as a SOD homodimer) are possible mechanisms of pathogenesis. It is also possible that mutant SOD polypeptides decrease or, in rare instances, increase the activity of the enzyme. These alterations in activity level may occur when the mutant SOD is either present as part of a heteromeric complex including mutant and wild-type SOD subunits or as homomeric mutant subunit complex.

i) Administration of SOD Polypeptides

Wild-type SOD polypeptides may be administered to patients with a dominant negative SOD mutation which lowers effective SOD levels in the affected tissue.

Mutant ALS SOD polypeptides identified in FALS patients or created in the laboratory and different from those present in the affected individual may be administered to patients with either dominant negative or gain of function type SOD mutations. Useful polypeptides for this method of complementation are those which, when added to the SOD polypeptide isolated from the affected patient, negates the alteration in SOD physical or enzymatic activities conferred by the mutant SOD polypeptide.

Administration of mutants with increased SOD activity may be used as a method of treating individuals with lowered SOD activity. Such mutants may be naturally occurring, e.g., FALS polypeptides, or constructed in the laboratory. For example, those mutants described by Parge et al. (P.N.A.S. 89:6109–6113 (1992)) or Getzoff et al. (Nature 358:347–351 (1992)) may be used. FALS polypeptides or nucleic acids altered in the laboratory for therapeutic use may also be administered.

Proteins in which the SOD polypeptide is fused to a ligand may be used for the purpose of stabilizing and/or targeting the useful SOD polypeptides. A fusion protein consisting of a SOD polypeptide, fused to, for example, tetanus toxin, calcium channel blocking agents, transferrin, poliovirus epitopes, neuropeptide fragments, or steroid hormone androgens, or a fragments thereof which are sufficient to target the SOD polypeptide to the motor neurons of an ALS patient may be used.

Proteins which are part of the SOD biochemical pathway may be administered as therapeutics for diseases of cell death, particularly ALS and FALS.

ii) Administration of Antioxidants

In the SOD biochemical pathway, a decrease in SOD activity results in an increase in the concentration of $O_2$ and an increase in SOD activity results in an increase in HO (see FIG. 7). Because either an increase or a decrease in SOD activity leads to an increase in free radicals, any antioxidant compound has potential therapeutic value for the treatment of ALS.

Antioxidants may be provided alone or in combinatio with SOD polypeptide or gene therapies. Because mutant SOD may cause free radical toxicity for the cells, those antioxidants which do not directly address the imbalance caused by SOD mutant peptides may still be useful therapies or adjunct therapeutics. Useful antioxidants include, for example, vitamin C, vitamin E, lycopene, bilirubin, urate, glutathione, dimercaprol, lutein, ubiquinol-10, dithiothretol, a mercaptan, a sulfa compound, methionine, cysteine or N-acetyl cysteine. For example, Vitamin E, Vitamin C, lazaroids (Upjohn, Kalamazoo), BHA, BHT, and beta-carotene are all useful therapeutics.

iii) Administration of Chelating Agents

Chelating agents, e.g., desferoxamine, known to chelate transition metals involved in the SOD biochemical pathway may be administered for the treatment of a disease involving a mutant SOD gene, e.g., ALS or FALS. For example, EDTA, EGTA, DETC, BCDA, penicillamine, a metallothionein protein, or a apo-metal binding protein, yeast copper metallothionein, apo-superoxide dismutase, hemoglobin, myoglobin, or plastocyanin.

iv) Administration of Monoclonal Antibodies to SOD Polypeptides

Monoclonal antibodies which are specific for the mutant SOD polypeptide may be administered for the treatment of any diagnosed sporadic or familial case of ALS. Polyclonal and monoclonal antibodies which recognize the mutant SOD polypeptide may be obtained using standard techniques known in the art. These antibodies may be subtractive techniques, e.g., by raising polyclonals against mutant SOD, removing those antibodies reactive with normal SOD, and using the remaining antibodies for the preparation of a reagent. The useful monoclonal antibody is an antibody which partially or fully restores the SOD enzymatic activity to the appropriate level in the patient. The desirable antibody may be identified as that antibody which restores SOD levels to within 40% of wild-type levels. Monoclonal antibodies may be tested in vitro by assaying the enzymatic activity of the SOD isolated from a patient in the presence and absence of the monoclonal antibody. Useful antibodies may be used specifically to eliminate the activity of the mutant SOD. This approach utilizes monoclonal antibodies specifically reactive with the mutant polypeptide. In the alternative, when the disease symptoms are the result of excess SOD activity, antibodies to both wild-type and mutant SOD polypeptides are therapeutically useful.

v) Administration of Anti-sense RNA

Patients diagnosed with a disease in which a causative agent is a mutant SOD gene may be treated by the administration of anti-sense RNA which is complementary to the mutated region of the SOD gene are anti-sense RNA to wild-type SOD. These anti-sense RNA therapeutics may be synthesized using standard techniques to develop anti-sense RNA therapeutics. Anti-sense RNA which recognizes the mutant sequences may be administered for all genetic forms of SOD disease resulting from a SOD mutation. Anti-sense RNA which recognizes wild-type SOD may be administered to reduce levels of SOD enzymatic activity when the disease is a result of excess SOD.

vi) Administration of Inhibitors of SOD

Where the disease is due to an increase in SOD activity, inhibitors of SOD may be administered. For example, peptides derived from wild-type or mutant SOD, non-peptide analogs of SOD, or any small molecule inhibitor of SOD, e.g., diethyldithiol carbamate (Dury et al., *PNAS* 89:9715–9719, 1992) or bathocurpronine disulfonic acid may be administered.

vii) Genetic Therapy for FALS

Therapeutic Administration of SOD1, SOD2, or SOD3 Coding Sequences in a Viral Vector.

Retroviral vectors, or other viral vectors with the appropriate tropism for cells affected by the defective SOD gene, e.g. motor neurons involved in ALS, may be used as a gene transfer delivery system for the SOD1, SOD2, or SOD3 genes which encode therapeutic SOD polypeptides. The useful polypeptides to be encoded are described above. Numerous vectors useful for this purpose are generally known (Miller, Human Gene Therapy 15–14, 1990; Friedman, Science 244:1275–1281, 1989; Eglitis and Anderson, *BioTechniques* 6:608–614, 1988; Tolstoshev and Anderson, *Current Opinion in Biotechnology* 1:55–61, 1990; Sharp, *The Lancet* 337:1277–1278, 1991; Cornetta et al., *Nucleic Acid Research and Molecular Biology* 36:311–322, 1987; Anderson, Science 226:401–409, 1984; Moen, *Blood Cells* 17:407–416, 1991; and Miller and Rosman, *Biotechniques* 7:980–990, 1989; Le Gal La Salle et al., Science 259:988–990, 1993). Retroviral vectors are particularly well developed and have been used in a clinical setting (Rosenberg et al., *N. Engl. J. Med* 323:370, 1990). In the case of ALS and FALS, poliovirus and herpes virus vectors, which infect neurons, are particularly useful.

The therapeutic SOD polypeptide may also be administered via a retroviral vector which incorporates into the hematopoetic cells, effectively administering the SOD polypeptide systemically in the presence or absence of targeting sequences.

The retroviral constructs, packaging cell lines and delivery systems which may be useful for this purpose include, but are not limited to, one, or a combination of, the following: Moloney murine leukemia viral vector types; self inactivating vectors; double copy vectors; selection marker vectors; and suicide mechanism vectors.

Fragments or derivatives of the Cu/ZnSOD, mSOD, or ecSOD polypeptides may also be administered by retroviral gene transfer therapy or another suitable viral vector system. Useful fragments or derivatives of SOD1, SOD2, or SOD3 may be administered by inserting the nucleic acids encoding these fragments or derivatives in place of the complete SOD gene in a gene therapy vector, as described above. Such constructs may be tested using the methods for testing the effects of CuZnSOD, mSOD, or ecSOD on ALS related enzymatic alterations, as described above.

Non Viral Methods for the Therapeutic Delivery of Nucleic Acid Encoding Cu/ZnSOD, mSOD, or ecSOD.

Nucleic acid encoding Cu/ZnSOD, mSOD, or ecSOD, or a fragments thereof, under the regulation of the wild-type promotor and including the appropriate sequences required for insertion into genomic DNA of the patient, or autonomous replication, may be administered to the patient using the following gene transfer techniques: microinjection (Wolff et al., *Science* 247:1465, 1990); calcium phosphate transfer (Graham and Van der Eb, *Virology* 52:456, 1973; Wigler et al., *Cell* 14:725, 1978; Felgner et al., *Proc. Natl. Acad. Sci. USA* 84:7413, 1987); lipofection (Felgner et al., *Proc. Natl. Acad. Sci. USA* 84:7413, 1987; Ono et al., *Neuroscience Lett* 117:259, 1990; Brigham et al., *Am. J. Med. Sci.* 298:278, 1989; Staubinger and Papahadjopoulos, *Meth. Enz.* 101:512, 1983); asialorosonucoid-polylysine conjugation (Wu and Wu, *J. Biol. Chem.* 263:14621, 1988; Wu et al., *J. Biol. Chem.* 264:16985, 1989); and electroporation (Neumann et al., *EMBO J.* 7:841, 1980).

V. ADMINISTRATION OF COMPOUNDS TO PREVENT THE ONSET OF SYMPTOMATIC FALS

In a patient diagnosed to be at risk for FALS any of the above therapies may be administered before the onset of symptomatic ALS.

VI. ADMINISTRATION OF SOD MUTANT POLYPEPTIDES FOR TREATMENT OF NEOPLASMS

Cytotoxic mutant SOD polypeptides can be used to treat neoplasms. Such cytotoxic compounds may be administered using any of the known methods for administering cancer chemotherapeutic agents.

VII. TREATMENT OF SPORATIC ALS CAUSED BY ENVIRONMENTAL FACTORS

All therapeutic approaches described herein which alter SOD enzymatic levels or affect reactant or product levels within the SOD biochemical pathway but do not hinge on specific characteristics of the mutant polypeptide, may be used with sporadic ALS which is not the result of a genetic defect.

VIII. DIAGNOSIS AND TREATMENT OF DISEASES RESULTING FROM MUTATIONS IN GENES ENCODING NON-SOD POLYPEPTIDES OF THE SOD BIOSYNTHETIC PATHWAY

Diseases caused by deleterious mutations in other polypeptides normally active in the SOD biosynthetic pathway, e.g., catalase, glutathione peroxidase, and nitric oxide synthase, may be diagnosed and treated using the above methods. The above treatments alter SOD activity and the administration of therapies which alter SOD activity will restore the imbalance caused by the perturbations elsewhere in the pathway.

The following examples are to illustrate not limit the invention.

EXAMPLES

I. Identification of the Causative Gene in Familial ALS

Described here is the identification of fourteen different SOD1 missense mutations in sixteen different FALS families. Additionally, mutations have been detected by SSCP but not sequenced in five families.

A) Methods

Methods: PCR primers are used in the analysis of SOD1 were:

```
Exon 2:

Set a    5' ACTCTCTCCAACTTTGCACTT 3'    5'CCCACCTGCTGTATTATCTCC 3'

Set b    5' TTCAGAAACTCTCTCCAACTT 3'    5'CGTTTAGGGGCTACTCTACTGT 3'

Exon 4:

Set a    5' CATATAAGGCATGTTGGAGACT 3'   5' TCTTAGAATTCGCGACTAACAATC 3'

Set b    5' CATCAGCCCTAATCCATCTGA 3'    5' CGCGACTAACAATCAAAGTGA 3'
```

PCR amplification was performed on Perkin Elmer Cetus or MJ Research thermal cyclers. The program for amplification was as follows: 2 minutes, 95° C. initial denaturation; 1 minute each at 95° C., 60° C. and 72° C., entrained for 32 cycles; 6 minutes at 72° C. final extension. The expected product sizes for exons 2 and 4 are respectively 132 and 214 bp for primer sets a, and 207 and 236 for primer sets b. SSCP analysis was performed using MDER gels using the manufacturer's recommended protocol (J. T. Baker). Gels containing 5% glycerol were run at room temperature at 4 W for 16 hours. Gels were dried and exposed to film for autoradiography. Sequencing of PCR-amplified exon DNA was performed by purifying the resulting product with Centracon columns (Amicon) and directly sequencing the DNA using Sequenase kits (U.S. Biochemicals).

B) Demonstration of Linkage

A CA-dinucleotide repeat D21S223 has been identified in cosmid 21–4.25 from the FALS-linked region.

Using the CA-dinucleotide repeat in Cosmid 21–4.25 from the FALS-linked region we have now found that exon 2 of SOD1 can be amplified by the polymerase chain reaction (PCR) from this cosmid. This indicates very close proximity of D21S223 and the SOD1 gene. We have confirmed the linkage of D21S223, and therefore SOD1, to FALS: D21S223 produces the highest lod scores yet detected (Table 1). Using the program HOMOG (Ott et al. *J. Am. J. Hum. Genetics* 28:528–529, 1976; Ott *Analysis of Human Genetics* 203–216, 1991), we have identified a subset of six of these FALS families in which the disease displays no recombination with D21S223 (Table 1, z=6.8 at theta=0) and is likely to be tightly linked to SOD1; nine additional families have also been shown to display significant linkage to the SOD1 region of chromosome 21.

C) Design of PCR Primers and SSCP Analysis

Figures 1, 1A:
FIGS. 1B–1 and 1B–2 are sequence analyses of SOD1 exons 2 and 4 in genomic FALS DNA.
Figures 1, 1A, 2:
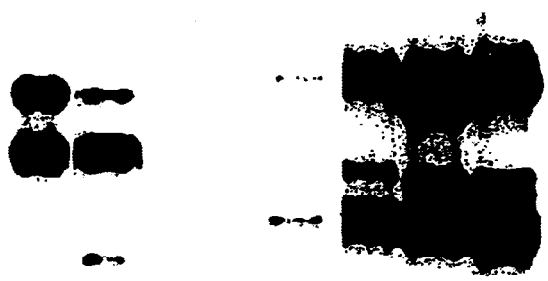

To determine if FALS is associated with mutations in the SOD1 gene, PCR primers were designed for two of the five SOD1 exons based on the published sequence for human SOD1 (Levanon et al., EMBO J. 77–84, 1985; Hallewell et al., *Superoxide Dismutase in Chemistry, Biology and Medicine* 249–256, 1986). These primers were used for PCR amplification of SOD1 exonic DNA from genomic DNA of normal, control individuals and of single FALS-affected individuals from families tightly linked either to SOD1 or neighboring markers on chromosome 21q. The products of the PCR reactions were denatured and separated on a polyacrylamide gel (0.5×MDE, J. T. Baker) for single-strand conformational polymorphism (SSCP) analysis, which detects mobility shifts of single-strand DNA caused by sequence variations (Orita et al., *Genomics* 5:874–879, 1989). Autoradiograms of these gels revealed shifts in band mobility for 6 of the 15 families linked to the SOD1 region of chromosome 21q. An additional 12 FALS families also revealed anomalous SSCPs; these families were too small for significant linkage analysis. Five of the FALS families are excluded from linkage to chromosome 21q (table 2); none showed abnormal SSCPs. FIG. 1*a* shows the data for SSCP analysis of SOD1 exons amplified by PCR from lymphocytes of normal and FALS-affected individuals. Specifically FIG. 1A is an autoradiogram showing variations in single-strand conformational banding patterns between normal and FALS DNA for SOD1 exons 2 (top) and 4 (bottom). "N" designates lanes with DNA from normal individuals. The numbers designate lanes with FALS DNA samples and correspond to family numbers in panel B and in Table 3. No band shifts were detected in control DNA samples from normal individuals (140 and 112) respectively for exons 2 and 4 (Table 2).

SSCP analysis was then performed on all available DNA samples from members of families 3, 11, and 192C. In each family, all affected individuals displayed the same band pattern as the originally characterized FALS patient. Additionally, in other family members determined by haplotype analysis to be at risk for FALS, the FALS haplotype cosegregated with the distinctive SSCP variant.

D) Sequencing of SOD1 in Affected Families Direct sequencing of PCR-amplified DNA from exons 2 and 4 was performed for 16 of the 23 FALS families with anomalous SSCP bands. In each instance, there was heterozygosity in the DNA sequence indicative of one normal and one abnormal chromosome. As summarized in Table 3, we identified single base pair changes in all 13 of these families. These 13 mutations predict eleven distinct amino acid substitutions. Two different amino acid substitutions were detected in each of two codons (41 and 93; Table 3). In each of two codons (37 and 113), two apparently unrelated families have the same mutation. The same mutation in codon 93 was detected independently in two branches of the same family (designated 3 and 3-192C, Table 3).

Figures 1, 1B:
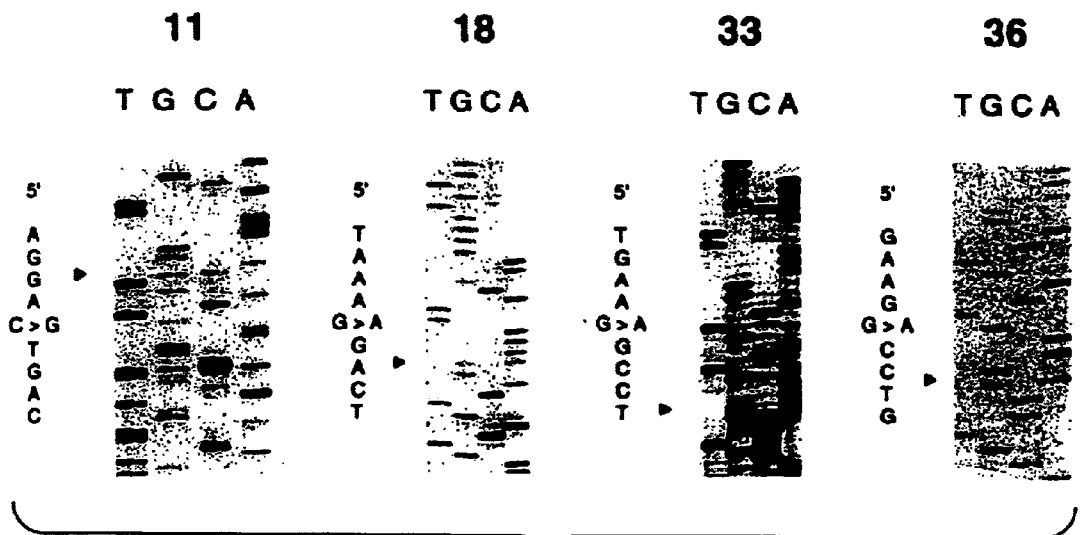
Figures 1, 1B, 2:
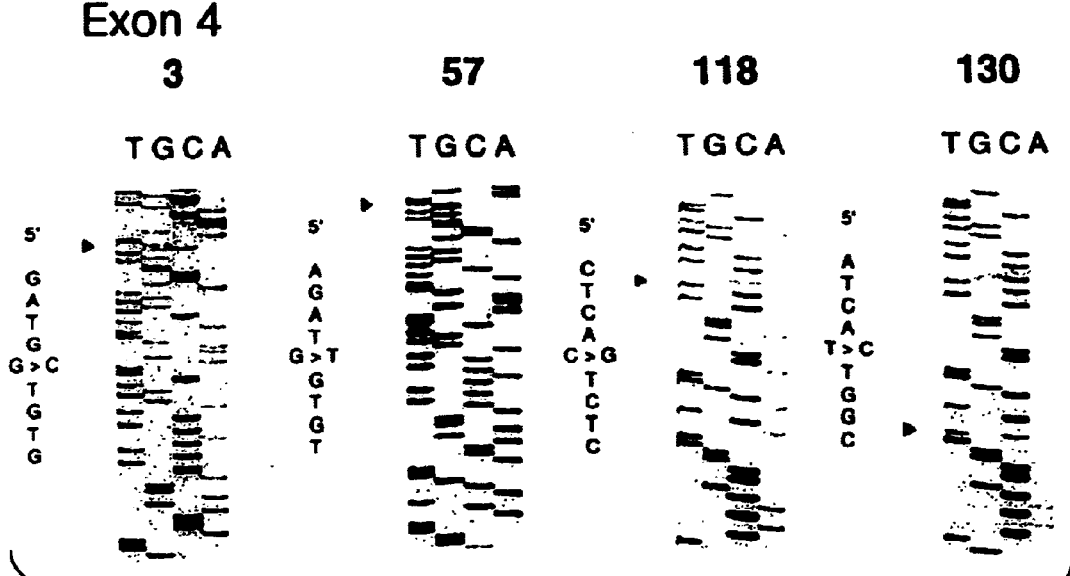

Representative data is shown in FIG. 1B. FIG. 1B are sequence analysis of SOD1 exons amplified by PCR from genomic DNA from lymphocytes of normal and FALS-affected individuals specifically shown in sequence analysis of SOD1 exons 2 and 4 in genomic FALS DNA; the numbers above each sequence ladder identify the affected family, corresponding to family numbers in panel A and in Table 3. The vertically oriented sequence to the left of each ladder designates nine base pairs of sequence including the mutation, indicated by a double base pair, with the wild-type base on the left; the arrowhead denotes the position within the sequence showing heterozygosity as indicated by two (normal and FALS) base pairs. Sequence ladders read 5'->3' from top to bottom.

Nine of the eleven sequence changes alter recognition sites for restriction enzymes (Table 3). For example, in family 11, a new MaeIII site (GTNAC) results from the C→G transition (normal sequence CTGAC). To confirm these sequence changes, we digested PCR products of the corresponding exons with the appropriate restriction enzymes. MaeIII digestion of the exon 2 PCR product for affected members of family 11 produced three bands on a denaturing acrylamide gel (Sequagel 6 (National Diagnostics)): a 132 bp full length product and products of 72 and 60 bp, the fragment sizes expected given the extra MaeIII site in the mutant DNA. These fragments were not detected in normal, control DNA samples from 70 unrelated members of our ALS families or from 73 unrelated members of reference pedigrees in the Centre d'Etude du Polymorphiseme Humain (CEPH, (Dausset et al., *Genomics* 6:575–577, 1990)). The base pair changes in families 3, 118, 130 and 684C introduce other novel restriction sites; additionally, in families 33, 36, 130, and 684C the single-base changes eliminate restriction sites normally present in SOD1.

These changes occur in all 13 of these families.

These 13 mutations predict eleven distinct amino acid substitutions. Two different amino acid substitutions were detected in each of two codons (41 and 93; Table 3). In each of two codons (37 and 113), two apparently unrelated families have the same mutation. The same mutation in codon 93 was detected independently in two branches of the same family (designated 3 and 3–193C, Table 3).

These studies identify eleven single amino acid 5 changes in SOD1 based upon the genomic DNA sequences of members of thirteen different FALS families. These changes were not detected in more than 100 chromosomes from normal individuals and thus it may be concluded that these mutations are not simply normal allelic variants. Instead, these mutations occur in tight association with FALS. It is concluded that the mutations identified herein in the SOD1 gene are the mutations which cause FALS.

II. Identification of an ala 4 to val Mutation

We screened exon 1 of SOD1 in DNA from 167 FALS pedigrees using single-strand conformational polymorphism (SSCP) analysis (Orita et al. (1989) *Proc. Natl. Acad. Sci. USA* 86, 2766–2770; Orita et al. (1989) *Genomics* 5, 874–879) (FIG. 8A). Identical variant exon 1 SSCP patterns were detected in 14/172 FALS families (designated as families #20 45, 103, 104, 114, 125, 127, 156, 160, 176, 189, 221, 224, 228, and 233). No other variant SSCP patterns were seen in the DNA encoding exon 1 in the other 159 FALS families or in 130 patients with sporadic ALS. A different SSCP band shift was observed in a single normal individual in a total of 116 assayed, but determination of the DNA sequence revealed that this shift was not caused by a change in the coding region for exon 1. As shown in FIG. 8B, DNA sequence analysis revealed a C-to-T transition at base pair 14 of SOD1 exon 1 in affected individuals with abnormal SSCPs. This missense mutation predicts a valine for alanine substitution at codon 4. The C-to-T mutation eliminates restriction enzyme sites for Mwo I ($GCN_7GC$) and Hae III (GGCC). Thus, when the mutation is present, Hae III digestion of the above exon 1 PCR product produces fragments of 38, 49, and 95 base pairs; by comparison, without the mutation, the expected fragments are 24, 25, 38, and 95 base pairs. Similarly, when the mutation is present, Mwo I does not digest the 182 bp exon 1 PCR product whereas without the mutation, digestion with this enzyme produces fragments of 71 and 111 bp. Ala 4 is highly conserved in the SOD1 enzyme of many species (Levanon et al. (1985) EMBO J. 4, 77–84; Cannon et al. (1987) Isozymes Curr. Top. Biol. Med. Res. 14, 73–81; Hjalmarsson et al. (1987) Proc. Natl. Acad. Sci. USA 84, 6340–6344; Perl-Treves et al. (1988) Plant Mol. Biol. 11, 609–623; Montesano et al. (1989) Eur. J. Biochem. 186, 421–426; Seto et al. (1989) Gene 75, 85–92; Chary et al. (1990) J. Biol. Chem. 265, 18961–18967; Benedetto et al. (1991) Gene 99, 191–195; Hallewell et al. (1991) Biochem. Biophys. Res. Commun. 181, 474–480) (8C) consistent with the hypothesis that this site is important for enzyme function. The restriction enzyme site changes associated with the SOD1Ala4 to Val mutation are summarized in Table 4.

The ala 4 to val mutation in the SOD1 gene is the most commonly identified mutation associated with FALS. We have identified 14 apparently independent occurrences of this mutation. This represents 14/36 or 38.9% of our FALS families with identified SOD1 mutations. Deng et al. ((1993) Science 261, 1047–1051) reported an additional eight occurrences in 17 FALS families with identified SOD1mutations. By comparison, the next most frequent mutations we have identified (Rosen et al. (1993) Nature 362, 59–62), gly 37 to arg and ile 113 to thr, have each been detected in two independent families. The ala 4 to val mutation is associated with a consistently severe clinical phenotype in terms of duration of survival after disease onset (Table 5). Patients with the ala 4 to val mutation survive only an average of 1.2 years after disease onset, as compared to 2.5 years for the average survival of all other FALS patents. by contrast, the age of onset in the exon 1 families is similar to that in other FALS patients. Thus, the ala 4 to val exon 1 mutation underlies an aggressive form of ALS.

Exon 1 PCR primers used for these SSCP studies were: 5'ATAAAGTAGTCGCGGAGACGG-3' (SEQ ID NO: 18) and 5'-GCCTTCTGCTCGAAATTGATG-3' (SEQ ID NO: 19). The expected product size is 182 bp. PCR amplification in Perkin Elmer Cetus or MJ Research thermal cyclers entailed initial denaturation (95° C., 2 min) and 32 cycles of 1 minute each at 95° C., 60° C., 72° C. and then 6 minutes at 72° C. for final extension. SSCP analysis was performed using MDE gels (J. T. Baker) with the manufacturer's recommended protocol. Sequencing of PCR-amplified DNA involved further purification of the products on Centricon columns (Amicon) and direct sequencing with a Sequenase kit (U.S. Biochemicals) using the above primers. Sequencing gels were prepared using Sequagel-6 (National Diagnostics) according to the manufacturer's recommended protocol.

III. Expression of SOD1 in ala to val individuals

The observation that SOD1 mutations are associated with FALS suggests that SOD1 may play an important role in motor neuron survival. Based on this hypothesis, we examined the expression of SOD1 in central nervous system tissues from normal individuals and three patients carrying the exon 1 ala 4→val mutation. In normal spinal cord, in situ hybridization with a 51-mer probe (SEQ ID NO: 20) from coding sequence unique to SOD1 revealed abundant expression of the mRNA for this protein in large neurons in the anterior quadrant (FIG. 9).

Consistent with this observation, immunostaining of normal spinal cord with a monoclonal antibody to human SOD1 showed diffuse expression of the protein throughout the grey matter of the spinal cord and marked prominence of expression in large neurons including motor neurons, Clarke's column neurons, and neurons within the posterior horn (FIG. 10 and data not shown). This staining appeared throughout the cytoplasm and nucleus and extended into the processes of the large neurons. We also observed prominent staining in large neurons in the motor cortex, including Betz cells (data not shown).

In two individuals with the ala 4 to val mutation, pronounced immunostaining of SOD1 in large neurons in Clarke's column and posterior horn was evident as in normal individuals (data not shown). However, in association with pre-terminal motor neuron deterioration, reduced staining was seen in the anterior horn of the spinal cord (FIG. 11), although staining with cresyl violet and anti-neurofilament antibody indicated the presence of a few residual motor neurons.

Quantitation indicated that the density of anterior horn cells as assessed by cresyl violet (CV), anti-neurofilament (SMI-32), and anti-SOD1 staining in tissue from these two patients with the exon 1 mutation was decreased by about 80% as compared to four non-FALS controls. In the FALS patients, the number of motor neurons staining with SOD1 antibody was only about two-thirds of the number stained by either cresyl violet or anti-neurofilament antibody.

To understand the functional consequence of the ala 4 to val mutation, we studied SOD1 enzyme activity in lysates of red blood cells from two FALS-affected females carrying this mutation. Red blood cell lysates from both sexes of two other groups were also studied: normal individuals with no known neurological diseases (18 males and 13 females) and individuals with sporadic ALS (SALS; 9 males and 6 females). The mean SOD1 activities for control females and males did not differ significantly (p=0.054 by ANOVA); in similar, more extensive analyses by others, no significant differences in RBC lysate SOD1 activity have been observed between males and females (S. Marklund, personal communication). We have therefore compared the female FALS SOD1 activities to the combined male and female SOD1 activities for the two other groups. The two female FALS patients with the ala 4 to val mutation showed statistically significant reductions in SOD1 enzymatic activity per mg total protein (Table 6) compared to specimens from 31 normal controls (p=0.014) and 15 SALS patients (p=0.013).

We also examined SOD1 activity in lymphoblastoid cell line established from a patient with this exon 1 mutation. To determine the effects of gene dosage of SOD1on corresponding enzymatic activity, we examined lymphoblastoid cell lines from individuals who were mono-, di- and trisomic for chromosome 21. In these cell lines, the relative SOD1 enzyme activity levels for the mono-, di-, and trisomic cell lines were approximately 1:2:3, respectively (Table 7). The cell line from the patient with the ala 4 to val mutation in SOD1 had a level of enzymatic activity roughly comparable to that in the monosomy 21 patient. Using the same lines, we performed Western immunoblots to gauge the relative levels of SOD1 protein. The observed overall protein levels of SOD1 in the mono-, di- and trisomic lines were roughly 1:2:3 (Table 7). The level of SOD1 protein in the exon 1 line was approximately half the normal level and was comparable to the monosomy 21 level. Thus, SOD1 activity per unit SOD1 protein was approximately normal in the lymphoblastoid line carrying the ala 4 to val mutation, although total SOD1 enzymatic and protein levels were only about one-half of normal.

Using cytosol from frontal cortex (Brodmann area 11), we determined SOD activities in three FALS patents with the ala 4 to val exon 1 mutation and 12 normal controls. Among the controls there was no significant sex difference, correlation of activity with age (r=−0.103), or postmortem interval (r=−0.100). SOD activity was reduced by 43.2% in the ala 4 to val FALS patients relative to the controls (p=0.015; Table 8). In a comparable brain sample from a single, age-matched FALS patient without a known SOD1 mutation, the SOD1 activity was 376 $SOD_{525}$ U/mg, a value that is not significantly different from that of controls (p=0.87).

A. SOD1 Enzymatic Activity

Three methods were used to determine SOD1 activity levels. For the brain tissue samples we quantified inhibition of spontaneous oxidation of epinephrine as a measure of SOD1 activity (Misra et al. (1972) *J. Biol. Chem.* 247, 3170–3175). The brain SOD activity was inhibited by 70–80% with 5 mM KCN. For the lymphoblastoid cell lines (Anderson et al. (1984) In Vitro 20, 856–858), we used a commercial assay (Randox Laboratories, Antrim, Northern Ireland) that employs xanthine and xanthine oxidase to generate superoxide radicals that interact with 2-(4-indophenyl)-3-(4-nitrophenol)-5-phenyltetrazolium chloride to form a red formazan dye. In this assay, SOD activity, detected spectrophotometrically at 505 nm, is measured by the degree of inhibition of this reaction. Erythrocyte lysates were prepared by chloroform:ethanol extraction (Winterbourn et al. (1975) *J. Lab. Clin. Med.* 85, 337–341). For the red cell lysates, two assays were used: the epinephrine autoxidation assay (Misra et al. (1972) *J. Biol. Chem.* 247, 3170–3175) and SOD-525 commercial assay kit (Bioxytech, Cedex, France) in which SOD1 initiates a reaction with a proprietary chromophore. One unit/mg in the SOD-525 assay corresponds to 369.8 units/mg by the epinephrine autoxidation assay. Differences between test groups were analyzed by analysis of variance (ANOVA) followed by Fisher's PLSD post-hoc test.(Zar, J. H. (1974) *Biostatistical Analysis*. Prentice Hall, Englewood Cliffs, N.J.).

B. Western Immunoblotting of SODS Polypeptide Proteins from crude cell extracts were separated by discontinuous SDS polyacrylamide gel electrophoresis (Laemmli, U.K. (1970) *Nature* 227, 680–685) using 12% (w/v) gels. The separated proteins were transferred by electroelution onto nitrocellulose as described (Towbin. et al. (1979) *Proc. Natl. Acad. Sci. USA* 76, 4350–4354). The nitrocellulose membrane was blocked with 5% non-fat dried milk in a Tris-buffered saline (TBS) for 30 minutes, followed by incubation in buffer A (1% non-fat dried milk, 0.2% Triton X-100 in TBS) containing the anti-(human SOD1) antibody for 90 minutes. The anti-(human SOD1) antibody was used at 1000:1 dilution. The membrane was washed in buffer A thrice for 5 minutes, then incubated for 1 hour in buffer A containing anti-mouse IgG-horseradish peroxidase conjugate (BioRad). The membrane was then washed in buffer A twice for 5 minutes, followed by TBS for 5 minutes. The membrane was incubated in ECL reagents (Amersham) for 1 minute, sealed in plastic wrap, and placed on X-ray film for 15–120 seconds. Films were scanned using a Helena Labs Quick Scan densitometer. Several exposures were used and several protein concentrations analyzed to permit integration within the linear range of film exposure.

C. In Situ Hybridization

Human spinal cords were removed one hour post-mortem, frozen on dry ice and kept at −80° C. until sectioning. Later 12 Am thick frozen sections were cut using a cryostat and fixed for 5 minutes with 4% paraformaldehyde in phosphate buffered saline (PBS) pH 7.4, then treated with 0.25% acetic anhydride in 0.1 M triethanolamine, 0.9% NaCl pH 8.0 for 10 minutes. Following dehydration in increasing concentrations of ethanol, lipids were extracted from the sections with chloroform and air dried. Hybridization reactions were performed in 50% formamide, 4X, SSC (1×SSC=0.15 M NaCl, 0.15 M sodium citrate pH 7.2), 0.02% Ficoll, 0.02% polyvinylpyrrolidone, 0.02% bovine serum albumin, 500 μg/ml sheared single-stranded salmon sperm DNA, 250 μg/ml yeast tRNA, 10% dextran sulphate and 50 mM dithiothreitol for 16 hours at 37° C.

Slides were rinsed in 1×SSC and washed for four 15 minute intervals in 2×SSC, 50% formamide at 40° C., followed by two 60 minute rinses in 1×SSC at 25° C. The sections were briefly rinsed in distilled water, 70% ethanol, and 95% ethanol and then air dried for autoradiography. The sections were coated with Kodak NTB3 nuclear track emulsion and developed after 2 weeks. Toluidine blue was used as a background stain. The sequence of the 51-mer oligonucleotide, derived from the human SOD1 gene, is 5'ATGCAGGCCTTCAGTCAGTCCTTTAAT-GCTTCCCCACACCTTCACTGGTCC3' (SEQ ID NO: 20). Hybridization with the sense probe did not result in any specific labeling.

D. Immunohistochemistry

Brains were blocked freshly at the time of autopsy and flash frozen in liquid nitrogen or fixed in periodate lysine paraformaldehyde for 48 hours at 4° C., followed by cryoprotection in 20% glycerol, 2% dimethylsulfoxide in phosphate buffer and sectioning at 50 μm on a sledge microtome. Sections were washed in cold 0.1M PBS pH 7.3, incubated in 10% normal goat serum in PBS, and placed in dilute monoclonal antibody specific for human Cu/Zn superoxide dismutase (Sigma, clone SD-G6, 1:20–1:100) or nonphosphorylated neurofilament (SMI 32, Sternberger Monoclonals, 1:2000) in 5% normal goat serum and 0.3% Triton X-100 overnight at room temperature on a rocker. The next day sections were washed several times in PBS and incubated in 0.05% diaminobenzidine tetrahydrochloride in 0.005% hydrogen peroxide in Tris-HCl buffer pH 7.5 and monitored by intermittent microscopic examination. The peroxidase reaction was terminated by washes in PBS. Sections were mounted, air dried, and coverslipped. Other sections were stained with cresyl violet. The time to autopsy and the state of autopsied tissue did not differ between FALS and control samples; thus, assessment of cresyl violet-stained sections from non-motor regions (sensory cortex in brain; dorsal horn in spinal cord) revealed no obvious differences between normal and FALS tissues.

All motor neurons in each section stained with cresyl violet, anti-SOD-1, and anti-neurofilament were counted and their density expressed per anterior horn. Quantitative data were obtained from spinal cords and two FALS patients with the exon 1 mutation and six normal individuals. The number of motor neurons stained with cresyl violet (CV) and SMI32 and SOD1 antibodies were counted in each anterior horn in each section. Multiple sections were counted in each case. From these sections, the average number of motor neurons per anterior horn per section was calculated. Statistical analysis was performed using unpaired t-test and one factor ANOVA.

E. Mechanism of Mutant SOD1 Pathogenesis

The above-mentioned results show that a missense mutation in exon 1 of the SOD1 gene is found in association with FALS. This ala4 to val substitution is the most common single SOD1 mutation we have detected. We have not detected any SOD1 mutations in over 100 controls and 100 sporadic ALS (SALS) patients. The association of SOD1 mutations with FALS suggests that wild-type SOD is important for the long-term function and viability of neurons, particularly motor neurons. It is possible that normal SOD expression is required in non-neuronal cells, particularly glial cells, for example astrocytes; microglia; interneurons or immune system cells.

The SOD1 Ala4 to val mutation reduced total activity by 50% compared to normal controls. The exon 1 SOD1 ala4 to val gene mutation may be an antimorphic or dominant-negative gene mutation; a gain-of-function or neomorphic gene mutation; or a loss-of-function or a haplo-insufficient gene mutation. Each of these possibilities may result in a mutant SOD1 protein that does not normally remove oxygen free radicals, or produces uncommon, toxic oxygen species.

It is also possible that reduction or loss of normal SOD1function leads to a FALS phenotype via abnormal copper binding. For example, if the copper-binding site of SOD1 (a Cu/Zn enzyme) has reduced metal affinity, copper ion levels may elevate to toxic levels. Copper is a known neurotoxin (Scheinberg, (1988) In: Bondy et al. (eds) *Metal Neurotoxicity*, CRC Press, Boca Raton, Fla., pp. 55–60) and can participate in a variety of redox reactions to generate toxic-free radicals (Halliwell et al., (1992) In: *Scandalios (ed) Molecular Biology of Free Radical Scavenging Systems*, Cold Spring Harbor Laboratory Press, Cold Spring Harbor, N.Y., pp. 47–67), administration of copper chelating agents may prove efficacious in preventing or reducing the severity of FALS, SALS, or any other neurodegenerative diseases described herein.

III. Additional Exon 3 and Exon 4 Mutations in SOD1

Single-strand, conformational polymorphism (SSCP) analysis of SOD1 exon 4 revealed an altered banding pattern for an asymptomatic individual in family 202 whose identical twin had previously died from. ALS. Additionally, an altered SSCP pattern was observed for a FALS patient in family 212.

These variant SSCP bands were not seen in DNA samples from 168 other FALS patients, 169 sporadic ALS patients, and 100 normal controls.

DNA sequence analysis of exon 4 for these FALS patients revealed single base pair substitutions at codon 93 (GGT to GAT) in family 212 and codon 112 (ATC to ACC) in family 202 (FIG. 12). These changes create glycine 93 to aspartic acid and isoleucine 112 to threonine missense mutations in SOD1 in these FALS patients. The codon 112 mutation leads to a loss of an Sfa NI restriction enzyme site normally present in the wild-type SOD1 sequence of exon 4. Both mutations are in highly conserved amino acids.

We have also found a polymorphism in intron 3 of the SOD1 gene. SSCP analysis revealed its presence in 7 of the 157 FALS samples and 11 of 100 normal controls. DNA sequence analysis of the proximal segment of intron 3 revealed an A-to-C substitution 34 base pairs downstream of exon 3, counting from the G in the GT splice donor site (FIG. 13). Allele frequencies for the two forms of the intron 3 polymorphism are 94.5% for the A-containing allele and 5.5% for the C-containing allele. The heterozygosity (Ott, *Analysis of Human Genetics*, (1991) Johns Hopkins University Press, Baltimore, pp. 25–27) of these two allele polymorphism is 0.1. This A-to-C transversion in intron 3 creates novel sites for Hae II, Hha I and Hin PI restriction enzymes. The presence of the polymorphism in intron 3 was confirmed for all SSCP variants by restriction enzyme digestion of the PCR product (data not shown). The DNA sequence we have obtained in this region (FIG. 13) differs slightly from that previously published (Levanon et al., (1985) *EMBO J.* 4, 77–84; Hallewell et al., (1986) in *Superoxide and Superoxide Dismutase in Chemistry, Biology and Medicine*, ed. Rotilio, pp. 249–256).

We have performed SOD1 assays on red cell lysates from individuals with these mutations (Winterbourn et al., (1975) *J. Lab. Clin. Med.* 85, 337–341). In the individual with the G112T mutation, SOD1 activity was 2.8 U/mg total protein, which is less than the 10% confidence limits for the mean SOD1 activity (4.2±1.0 U/mg) of 31 individuals with no neurological diseases (P(Z=1.4)=0.081) (Zar et al., (1984) in *Biostatistical Analysis*, Prentice-Hall, Englewood, N.J., 2nd edition, pp. 83–86). In four individuals with the G93A mutation, SOD1 activity was 3.6+0.9 U/mg, which does not differ significantly from the 31 controls.

We note that survival in the G93A family (15 years in the index case) may be longer than in our other FALS families (mean 2.5 years, 99.9% confidence interval 8.8 years); by contrast, mean survival in two individuals with the G112T mutation was 0.9±0.1 years. These findings are consistent with the observation of Aoki and colleagues (*Nature Genetics* (1993) 5, 102–103) that FALS mutations producing the mildest loss of SOD1 function may cause the mildest forms of the disease.

These results are similar to those found with exon 1 SOD1 gene mutations, to the extent that a minor loss of SOD1 function results in a dominant phenotype. It is possible that some models (see above) which explain the phenotype of the Ala4→Val gene mutation in the SOD1 exon 1 may also apply to these exon 3 and exon 4 gene mutations.

IV. Effective Therapies for Preventing or Reducing the Severity of ALS

Each therapy may be used alone or in combination with one or more therapies as disclosed herein. The following formulations may be administered by any means described above.

A) Administration of an Antioxidant Formulation: One or more antioxidants may be administered in order to prevent or reduce the level of reactive free radicals, particularly oxygen free radicals; in a cell, particularly a motor neuron. For example, the diet may be supplemented with one or more of an antioxidant, preferably, vitamin C (ascorbate), vitamin E (alpha tocopherol), beta-carotene, lycopene, bilirubin, urate, glutathione, dimercaprol, lutein, ubiquinol-10, dithiothretol, mercaptans, preferably mercaptoethanol, sulfa compounds (i.e., the sulfonamides), for example, sulfa antibiotics such as N-sulfanilylbenzamide, amino acids or derivatives thereof, such as methionine, cysteine, or N-acetyl cysteine. Methods of administration and preferred dosages have been disclosed by Greengard (P. Greengard, in *The Pharmacological Basis of Therapeutics*, Goodman, L. S. and Gilman, A. 5ed. (1975); herein incorporated by reference). For compounds and methods of administration not disclosed in Greengard (supra), between 0.1 mg to 100 mg inclusive can be administered per day to an adult. Administration of an antioxidant formulation may be by any method disclosed herein. The actual dosage will depend on a number of factors, including the health of the individual patient and the progression of ALS. An antioxidant, as used herein, is any chemical capable of scavenging free radicals formed in a biological reaction.

B) Administration of a Drug Formulation: One or more drugs may be administered in order to prevent or reduce the level of reactive free radicals, particularly oxygen free radicals; in a cell, particularly a motor neuron. Drugs that are capable of inhibiting enzymatic systems which are associated with free radical production include deprenyl (a monoamine oxidase inhibitor) and the lazeroid compounds (inhibitors of lipid peroxidation). Dosages and methods of administrating deprenyl have been disclosed (Physician's Desk Reference 47 pg. 2351 (1993)). Clinical use of the lazeroid compounds has been discussed (J. M. McCall et al. Acta Anaesthesiol. Belg. 38, 417 (1987)). Administration of a drug formulation may be by any method disclosed herein. The actual dosage will depend on a number of factors, including the health of the individual patient and the progression of ALS.

C) Administration of an Enzyme Formulation: Direct intrathecal administration of one or more enzymes capable of scavenging free radicals can be performed in order to prevent or reduce the level of free radicals in a cell, particularly a motor neuron. For example, SOD-1 may be administered alone or in combination with one or more enzymes capable of scavenging free radicals, such as SOD-2, SOD-3, or catalase. The actual dosage of enzyme will depend on a number of factors, including the health of the individual patient and the progressive of ALS. Generally, 0.01 ug to 100 ug will be administered in a pharmaceutically acceptable formulation as described herein.

D) Administration of A SOD-1 Transgene: Functional copies of a SOD-1 gene into a cell, preferably a motor neuron cell, may be accomplished by delivery systems, for example viral vectors comprising portions of polio or herpes virus genomic DNA, retroviruses; or liposomes comprising targeting proteins or lipids. Methods for the therapeutic delivery of SOD-1 or other SOD genes are described herein.

E) Administration of Oligonucleotide Formulations: DNA oligonucleotides capable of binding with mutant SOD-1 mRNA may be designed. Preferably, the DNA oligonucleotide is at least 15 nucleotides, more preferably at least 25 nucleotides and most preferably at least 50 nucleotides in length. The DNA oligonucleotide is substantially homologous to the wild-type SOD-1 gene or is substantially homologous to any mutant SOD-1 gene described herein. The binding of one or more DNA oligonucleotides to a mutant SOD-1 mRNA will prevent protein translation of the mutant mRNA. Methods of administering a DNA oligonucleotide formulation have been described. The actual dosage of a DNA oligonucleotide formulation will depend on a number of factors, including the health of the individual patient and the progressive of ALS. Generally, 0.001 ug to 1oug will be administered in a pharmaceutically acceptable formulation as described herein.

F) Administration of a Metal Chelating Agent: Mutant SOD-1 function may modulate metal levels within a cell, for example, copper and/or zinc levels within a motor neuron. The administration of one or more metal chelating agents, preferably agents capable of chelating copper and/or zinc, may prevent or reduce the severity of ALS. Examples of chelating agents include EDTA (ethylenediamine tetraacetic acid), EGTA (ethleneglycol bis-beta-aminoethyl ether) N',N'-tetracetic acid), desferroxamine, DETC (diethyl-dithiocarbamate), BCDA (bathocurpronine disulfonic acid), and penicillamine, and tetracycline. (Miller, *Human Gene Therapy* 15–14, 1990; Friedman, *Science* 244:1275–1281, 1989; Eglitis and Anderson, *BioTechniques* 6:608–614, 1988; Tolstoshev and Anderson, *Current Opinion in Biotechnology* 1:55–61, 1990; Sharp, *The Lancet* 337:1277–1278, 1991; Cornetta et al., *Nucleic Acid Research and Molecular Biology* 36:311–322, 1987; Anderson, *Science* 226:401–409, 1984; Moen, *Blood Cells* 17:407–416, 1991; and Miller and Rosman, *Biotechniques* 7:980–990, 1989; Le Gal La Salle et al., *Science* 259:988–990, 1993). A metal chelating agent may also be a polypeptide, for example, a metallothionein protein, preferably yeast copper metallothionein; plastocyanin, apo-superoxide dismutase, or other apo-metal binding proteins. The administration of chelating agents and preferred dosages have been disclosed in Goodman and Gilman (The Pharmacological Basis of Therapeutics, 5Ed. Chapter 11, (1975); Physician's Desk Reference 47, pg 892 (1993)). For compounds and methods of administration not disclosed (supra), between 0.1 mg to 100 mg inclusive of a chemical chelating agent or between 0.01 ug to 100 ug of a polypeptide chelating agent can be administered per day to an adult. The actual dosage will depend on a number of factors, including the health of the individual patient and the progression of ALS. Administration of a metal chelating agent may be in the form of a therapeutic formulation as disclosed herein. The route of administration may be any route disclosed herein.

G) Administration of Peroxide-Reducing Polypentides: A key function of SOD is to detoxity the superoxide free radical (i.e., $O_2$) converting it to hydrogen peroxide (i.e., $H_2O_2$). In turn, hydrogen peroxide is converted to water by either catalase or glutathione peroxidase. Hydrogen peroxide itself can generate free radical more harmful than superoxide, for example the hydroxyl radical (ie. $OH^-$). Therefore, peroxide-reducing polypeptides capable of lowering the level of hydrogen peroxide in a cell, preferably a motor neuron, can be effective in preventing or reducing the severity of ALS. One or more peroxide-reducing polypeptides may be administered to a patient in order to prevent or reduce the severity of ALS. Examples of peroxide-reducing polypeptides include catalase, glutathione peroxidase, selenium dependent glutathione peroxidase, phospholipid hydroperoxide glutathione peroxidase, cytochrome c peroxidase, for example, the cytochrome c peroxidase from yeast mitochondra, ascorbate peroxidase, for example, ascorbate peroxidase from plants, NAD(P)H peroxidase, for example, from bacteria, guaiacol peroxidase, for example, from horseradish, ceruloplasmin, a polypeptide capable of exhibiting ferroxidase activity, the reductases, for example glutathione reductase, monodehydroascorbate reductase, or dehydroascorbate reductase.

A peroxide-reducing polypeptide may also be a "sacrificial" polypeptide which is capable of being reduced. The reduction of a sacrificial polypeptide would prevent or reduce reduction of key cellular polypeptides. Examples of sacrificial polypeptides include albumin, transferrin, ferritin, or any protein comprising thiol groups. Any method of administration disclosed herein may be used to administer a peroxide-reducing polypeptide. Preferably, the peroxide-reducing polypeptide is administered intrathecally in a dose range of between 0.01 ug to 100 ug per day to an adult. The actual dosage will depend on a number of factors, including the health of the individual patient and the progression of ALS.

Further embodiments are within the following claims.

TABLE 1

Linkage Analysis of FALS Pedigrees with SOD1 Marker D21S223 (DB1)

Lod Score

| Theta | 0 | 5 | 10 | 15 | 20 | 25 | 30 |
|---|---|---|---|---|---|---|---|
| All families[1] | -∞ | 3.83 | 4.25 | 4.05 | 3.55 | 2.87 | 2.11 |
| 21-linked families[2] | 6.80 | 6.05 | 5.26 | 4.44 | 3.61 | 2.77 | 1.93 |

[1]Data are tabulated from an analysis of 12 families in the Boston arm of the FALS collaborative study (7,11).
[2]A subset of six families with a high (>80%) posterior probability of linkage to D21S223 as defined using the program HOMOG (12). Some of the eleven mutations described in Table 3 were detected in DNA from members of FALS families too small for significant linkage analysis. Such families could not be included in the linkage data summarized in the Table.

TABLE 2

17 Single-Strand Conformational Polymorphisms in Exons 2 and 4 of SOD1 in FALS DNA[1]

|  | All FALS[2] | FALS-21[3] | Control[4] |
|---|---|---|---|
| EXON 2 |  |  |  |
| Normal | 148 | 15[5] | 140 |
| Variant | 7[6] | 1 | 0[7] |
| EXON 4 |  |  |  |
| Normal | 150 | 15 | 112 |
| Variant | 11[8] | 5 | 0 |

[1]See legend for FIG. 1 for Methods.
[2]Familial ALS
[3]Subset of families linked by HOMOG (12) to SOD1 (Boston) or adjacent markers (Chicago).
[4]DNA samples from normal individuals unrelated to members of FALS families.
[5]Six from Boston and nine from Chicago FALS pedigrees.
[6]Includes four, two and one samples respectively from Boston, Chicago and Montreal FALS pedigrees.
[7]12 control DNA samples revealed weak and somewhat variable SSCPs; all were normal by sequence analysis.
[8]Includes five, five and one samples respectively from Boston, Chicago and Montreal FALS pedigrees.

TABLE 3A

Base Pair Changes in SOD-1

| family | exon | amino acid | codon | new codon | new amino acid |
|---|---|---|---|---|---|
| 103 | 1 | ala4 | GCC | GTC | val |
| 104 | 1 | ala4 | GCC | GTC | val |
| 114 | 1 | ala4 | GCC | GTC | val |
| 127 | 1 | ala4 | GCC | GTC | val |
| 18 | 2 | gly 37 | GGA | AGA | arg |
| 594C | 2 | gly 37 | GGA | AGA | arg |
| 11 | 2 | leu 38 | CTG | GTG | val |
| 33 | 2 | gly 41 | GGC | AGC | ser |
| 36 | 2 | gly 41 | GGC | GAC | asp |
| 220C | 2 | his 43 | CAT | CGT | arg |
| 9967C | 4 | gly 85 | GGC | CGC | arg |
| 57 | 4 | gly 93 | GGT | TGT | cys |
| 3 | 4 | gly 93 | GGT | GCT | ala |
| 3-192C | 4 | gly 93 | GGT | GCT | ala |
| 37 | 4 | glu 100 | GAA | GGA | gly |
| 684C | 4 | glu 100 | GAA | GGA | gly |
| 118 | 4 | leu 106 | CTC | GTC | val |
| 130 | 4 | ile 113 | ATT | ACT | thr |
| 385C | 4 | ile 113 | ATT | ACT | thr |
| 78 | 5 | leu 144 | TTG | TCG | ser |
| 113 | 5 | ala 145 | GCT | ACT | thr |

TABLE 3B

SOD1 Mutations in Familial Amyotrophic Lateral Sclerosis

| Family | Base Pair Change | Amino Acid Change | Predicted Restriction Enzyme Change | PCR Product (bp)[1] | Restriction Fragments (bp) | |
|---|---|---|---|---|---|---|
|  |  |  |  |  | Normal | FALS-Specific[2] |
| Exon 2 |  |  |  |  |  |  |
| 18, 594C | GGA -> AGA | gly 37 -> arg |  |  |  |  |
| 11 | CTG -> GTG | leu 38 -> val | + MaeIII[3,4] | 132 | 132 | 72, 60 |
| 33 | GGC -> AGC | gly 41 -> ser | - HaeIII[5] | 132 | 83, 49 | 132 |
|  |  |  | - StuI | 132 | 83, 49 | 132 |
|  |  |  | - Eco57I | 132 | 97, 35 | 132 |

TABLE 3B-continued

SOD1 Mutations in Familial Amyotrophic Lateral Sclerosis

| Family | Base Pair Change | Amino Acid Change | Predicted Restriction Enzyme Change | PCR Product (bp)[1] | Restriction Fragments (bp) Normal | FALS-Specific[2] |
|---|---|---|---|---|---|---|
| 36 | GGC -> GAC | gly 41 -> asp | – HaeIII[3,5] | 132 | 83, 49 | 132 |
| 220C | CAT -> CGT | his 43 -> arg | – NlaIII | 132 | 87, 30, 9, 6 | 96 |

TABLE 3C

SOD1 Mutations in Familial Amyotrophic Lateral Sclerosis

| Family | Base Pair Change | Amino Acid Change | Predicted Restriction Enzyme Change | PCR Product (bp)[1] | Restriction Fragments (bp) Normal | FALS-Specific[2] |
|---|---|---|---|---|---|---|
| Exon 4 | | | | | | |
| 9967C | GGC -> CGC | gly 85 -> arg | + HinPI | 214 | 214 | 192, 22 |
|  |  |  | + HhaI | 214 | 214 | 192, 22 |
|  |  |  | + FspI | 214 | 214 | 193, 21 |
| 57 | GGT -> TGT | gly 93 -> cys |  | 214 |  |  |
| 3, 3-192C[6] | GGT -> GCT | gly 93 -> ala | + SfaNI[3] | 214 | 112, 100 | 72, 40 |
| 684C | GTT -> GGA | glu 100 -> gly | + Eco57I | 214 | 148, 66 |  |
|  |  |  | – MboII | 88, 68, 58 | 165 |  |
| 118 | CTC -> GTC | leu 106 -> val | + DdeI[3,4] | 214 | 120, 89, 5 | 83, 6 |
| 130, 385C | ATT -> ACT | ile 113 -> thr | + BsrI[3,4] | 214 | 124, 90 | 113, 11 |
|  |  |  | – BslI[3] | 214 | 116, 98 | 214 |
|  |  |  | – EaeI | 214 | 104, 57, 53 | 161 |

Based on primer sets a (see Figure Legend).
Other size products are predicted but not listed because they are not FALS-specific.
Predicted changes in indicated restriction fragments have been confirmed in genomic DNA from FALS patients.
The FALS MaeIII, DdeI and BsrI fragments were not seen in DNA respectively from 143, 73 and 73 control individuals.
All 73 DNA samples from normal controls showed the expected HaeIII restriction site.
The suffix C denotes families analyzed in Chicago. Families 3 and 3-192C are different branches of the same pedigree.

TABLE 4

Restriction Site Changes Associated with SOD1 Ala 4 to Val Mutation

| Base-pair change | Amino acid change | Predicted Restriction enzyme site lost | PCR product (bp)[1] | Restriction fragments (bp) Normal | FALS |
|---|---|---|---|---|---|
| GCG-> GTC | ala 4 ->val | Hae III (GGCC) | 182 | 95, 38, 25, 24 | 95, 49, 38 |
|  |  | Mwo I (GCN₇GC) | 182 | 111, 71 | 182 |

[1]size of PCR product using primers described in Methodology

TABLE 5

Age of onset and survival: ala 4 to val mutation vs other FALS pedigrees

|  | A4V FALS | All Other FALS |
|---|---|---|
| Survival |  |  |
| mean | 1.2 | 2.5 |
| n | 24 | 214 |
| std. dev. | 0.8 | 1.9 |
| Age of Onset |  |  |
| mean | 51.5 | 49.1 |
| n | 24 | 250 |
| std. dev. | 11.2 | 13.7 |

For survival, the difference between the two groups is significant at p<0.001 (student's t-test); the difference between the ages of onset is not significant. A4V designates the alanine 4 to valine substitution.

TABLE 6

Red blood cell lysate SOD1 enzymatic activity[1]

|  | A4V FALS | SALS[2] | Controls |
|---|---|---|---|
| Females |  |  |  |
| mean | 2.6 | 5.0 | 3.8 |
| n | 2 | 5 | 13 |

TABLE 6-continued

Red blood cell lysate SOD1 enzymatic activity[1]

|  | A4V FALS | SALS[2] | Controls |
|---|---|---|---|
| std. dev. Males | 1.0 | 0.9 | 0.7 |
| mean |  | 4.7 | 4.5 |
| n | 0 | 10 | 18 |
| std. dev. Total |  | 1.1 | 1.1 |
| mean | 2.6 | 4.8 | 4.5 |
| n | 2 | 15 | 31 |
| std. dev. | 1.0 | 1.1 | 1.0 |

[1] SOD units/mg total protein
[2] sporadic ALS

The p values for A4V FALS vs SALS and controls are 0.013 and 0.014, respectively (Student's t-test). For SALS vs control, the p value is 0.35.

TABLE 7

Lymphoblastoid cell line SOD1 enzymatic activity[1]

|  | A4V FALS | Monosomy[2] 21 | Normal 2 × 21 | Down's[2] 3 × 21 |
|---|---|---|---|---|
| SOD1 Activity | 0.026 | 0.021 | 0.052 | 0.091 |
| Relative SOD1 Protein[3] | 1.2 | 1.0 | 1.8 | 3.2 |
| Activity/relative SOD1 protein | 0.021 | 0.021 | 0.029 | 0.028 |

[1] SOD units/mg total protein
[2] karyotype analysis demonstrated that these lines are monosomic and trisomic for all of chromosome 21 (D. Patterson, personal communication)
[3] as assayed by Western blot

TABLE 8

Brain SOD1 activity[1]

|  | A4V FALS | Control |
|---|---|---|
| SOD1 Activity |  |  |
| mean | 223 | 392 |
| n | 3 | 12 |
| std. dev. | 33.5 | 100.3 |
| Age |  |  |
| mean | 41.3 | 71.3 |
| std. dev. | 2.1 | 14.3 |
| Sex Ratio (m/f) | 2/1 | 7/5 |
| Post-Mortem Interval |  |  |
| mean | 9.0 | 12.7 |
| std. dev. | 8.9 | 6.3 |

[1] $SOD_{525}$ units/mg total protein

The mean SOD1 activity for the A4V FALS patients and the controls differ significantly (p=0.015).

---

What is claimed is:

1. A transgenic mouse having somatic and germ cells containing a transgene, said transgene encoding and expressing a neurodegenerative disease-causing mutant SOD-1 polypeptide.

2. The mouse of claim 1, wherein said SOD-1 polypeptide is a murine SOD-1 poypeptide.

3. The mouse of claim 1, wherein said SOD-1 polypeptide is a human SOD-1 poypeptide.

4. The mouse of claim 1, wherein the disease causing polypeptide contains a Valine at position 4.

5. The mouse of claim 1, wherein the disease causing polypeptide contains a Valine at position 38.

6. The mouse of claim 1, wherein the disease causing polypeptide contains a Argine at position 41.

7. The mouse of claim 1, wherein the disease causing polypeptide contains a Valine at position 42.

8. The mouse of claim 1, wherein the disease causing polypeptide contains a Serine at position 44.

9. The mouse of claim 1, wherein the disease causing polypeptide contains an Aspartic acid at position 44.

10. The mouse of claim 1, wherein the disease causing polypeptide contains an Arginine at position 46.

11. The mouse of claim 1, wherein the disease causing polypeptide contains an Arginine at position 85.

12. The mouse of claim 1, wherein the disease causing polypeptide contains a Cysteine at position 93.

13. The mouse of claim 1, wherein the disease causing polypeptide contains Alanine at position 93.

14. The mouse of claim 2, wherein the disease causing polypeptide contains Glycine at position 100.

15. The mouse of claim 2, wherein the disease causing polypeptide contains Valine at position 106.

16. The mouse of claim 2, wherein the disease causing polypeptide contains Threonine at position 113.

17. The mouse of claim 1, wherein the expression of said mutant polypeptide is under the regulation of the wild-type promoter.

* * * * *

UNITED STATES PATENT AND TRADEMARK OFFICE
CERTIFICATE OF CORRECTION

PATENT NO. : 6,723,893 B1
DATED : April 20, 2004
INVENTOR(S) : Robert Brown, H. Robert Horvitz and Daniel R. Rosen It is certified that error appears in the above-identified patent and that said Letters Patent is hereby corrected as shown below:

Column 1,
Line 62, replace "*Neuroloay*" with -- *Neurology* --.

Column 2,
Line 52, replace "spatz" with -- Spatz --;
Line 64, replace "Greenfield" with -- (Greenfield --; and
Line 66, replace "180." with -- 180). --.

Column 3,
Line 28, replace "ha snow been" with -- has now been --.

Column 6,
Line 40, replace "and or" with -- and/or --.

Column 7,
Line 41, replace "reference)." with -- reference --; and
Line 45, replace "By." with -- By --.

Column 8,
Line 61, replace "omologous" with -- homologous --.

Column 10,
Line 56, delete "is an autoradiogram";
Line 58, replace "2(top" with -- 2 (top --; and
Line 59, replace "4(bottom" with -- 4 (bottom --.

Column 12,
Line 23, replace "ABNERMAL" with -- ABNORMAL --.

Column 13,
Line 32, replace "SOD1decrease" with -- SOD1 decrease --.

Column 15,
Line 32, replace "combinatio" with -- combination --.

Column 16,
Line 47, replace "Human Gene Therapy" with -- *Human Gene Therapy* --.

UNITED STATES PATENT AND TRADEMARK OFFICE
CERTIFICATE OF CORRECTION

PATENT NO. : 6,723,893 B1
DATED : April 20, 2004
INVENTOR(S) : Robert Brown, H. Robert Horvitz and Daniel R. Rosen It is certified that error appears in the above-identified patent and that said Letters Patent is hereby corrected as shown below:

Column 17,
Line 13, replace "CuZnSOD" with -- Cu/ZnSOD --; and
Line 18, replace "a fragments" with -- a fragment --.

Column 18,
Line 38, after "GCACTT 3'" insert -- (SEQ ID NO:6) --;
Line 38, after "ATCTCC 3'" insert -- (SEQ ID NO:7) --;
Line 39, after "CAACTT 3'" insert -- (SEQ ID NO:8) --;
Line 39, after "TACTGT 3'" insert -- (SEQ ID NO:9) --;
Line 41, after "GAGACT 3'" insert -- (SEQ ID NO:10) --;
Line 41, after "ACAATC 3'" insert -- (SEQ ID NO:11) --;
Line 42, after "ATCTGA 3'" insert -- (SEQ ID NO:12) --;
Line 42, after "AAGTGA 3'" insert -- (SEQ ID NO:13) --; and
Line 52, replace "MDER" with -- $MDE^R$ --.

Column 19,
Line 14, replace "EMBO J." with -- *EMBO J.* --; and
Line 51, "Direct" should begin on the next line.

Column 20,
Line 58, replace "#20 45" with -- # 45 --.

Column 21,
Line 13, replace "EMBO J." with -- *EMBO J.* --;
Line 31, replace "SOD1mutations" with -- SOD1 mutations --; and
Line 40, replace "by" with -- By --.

Column 22,
Line 56, replace "SOD1on" with -- SOD1 on --.

Column 23,
Line 16, replace "SODlmutation" with -- SOD1 mutation --; and
Line 47, replace "SODS" with -- SOD1 --.

Column 24,
Line 6, replace "Am" with -- $\mu$m --.

UNITED STATES PATENT AND TRADEMARK OFFICE
CERTIFICATE OF CORRECTION

PATENT NO. : 6,723,893 B1
DATED : April 20, 2004
INVENTOR(S) : Robert Brown, H. Robert Horvitz and Daniel R. Rosen It is certified that error appears in the above-identified patent and that said Letters Patent is hereby corrected as shown below:

Column 25,
Line 23, replace "SOD1function" with -- SOD1 function --;
Line 30, replace "*Scandalios* (ed)" with -- Scandalios (ed) --; and
Line 43, replace "from." with -- from --.

Column 27,
Line 34, replace "progressive" with -- progression --;
Line 61, replace "progressive" with -- progression --; and
Line 62, replace "loug" with -- 10$\mu$g --.

Column 28,
Line 42, replace "Polypentides" with -- Polypeptides --.

Column 70,
Line 26, before "mouse" insert -- transgenic --.

Signed and Sealed this

Seventeenth Day of May, 2005

JON W. DUDAS
*Director of the United States Patent and Trademark Office*

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
      (A) LENGTH: 2800 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: Xaa at position 5 is Ala or Val. Xaa at position 38 is Gly or Arg. Xaa at position 39 is Leu or Val. Xaa at position 42 is Gly, Ser or Asp. Xaa at position 44 is His or Arg. Xaa at position 86 is Gly or Arg. Xaa at position 94 is Gly, Cys or Ala. Xaa at position 86 is Gly or Glu. Xaa at position 107 is Leu or Val. Xaa at position 114 is Ile or Thr. Xaa at position 145 is Leu or Ser. Xaa at position 146 is Ala or Thr.

(xi) SEQUENCE DESCRIPTION: SEQ ID NO:1:

```
GAATTCTGCC AACCAAATAA GAAACTCTAT ACTAAGGACT AAGAAAATTG CAGGGGAAGA      60

AAAGGTAAGT CCCGGGATTG AGGTGTAGCG ACTTTCTATA CCCTCAGAAA ACTAAAAAAC     120

AAGACAAAAA AATGAAAACT ACAAAAGCAT CCATCTTGGG GCGTCCCAAT TGCTGAGTAA     180

CAAATGAGAC GCTGTGGCCA AACTCACGTC ATAACTAATG ACATTTCTAG ACAAAGTGAC     240

TTCAGATTTT CAAAGCGTAC CCTGTTTACA TCATTTTGCC AATTTCGCGT ACTGCAACCG     300

GCGGGCCACG CCCCCGTGAA AGAAGGTTG TTTTCTCCAC ATTTCGGGGT TCTGGACGTT      360

TCCCGGCTGC GGGGCGGGGG GAGTCTCCGG CGCACGCGGC CCCTTGGCCC CGCCCCCAGT     420

CATTCCCGGC CACTCGCGAC CCGAGGCTGC CGCAGGGGGC GGGCTGAGCG CGTGCGAGGC     480

GATTGGTTTG GGGCCAGAGT GGGCGAGGCG CGGAGGTCTG GCCTATAAAG TAGTCGCGGA     540

GACGGGGTGC TGGTTTGCGT CGTAGTCTCC TGCAGCGTCT GGGGTTTCCG TTGCAGTCCT     600

CGGAACCAGG ACCTCGGCGT GGCCTAGCGA GTT ATG GCG ACG AAG GYC GTG TGC     654
                                 Met Ala Thr Lys Xaa Val Cys
                                  1               5

GTG CTG AAG GGC GAC GGC CCA GTG CAG GGC ATC ATC AAT TTC GAG CAG      702
Val Leu Lys Gly Asp Gly Pro Val Gln Gly Ile Ile Asn Phe Glu Gln
     10              15                  20

AAG G CAAGGGCTGG GACGGAGGC TTGTGGTTGC GAGGCCGCTC CCGACCCGCT          756
Lys

CGTCCCCCCG CGACCCTTTG CATGGACGGG TCGCCCGCCA GGGCCTAGAG CAGGTTAAGC     816

AGCTTGCTGG AGGTTCACTG GCTAGAAAGT GGTCAGCCTG GGATTTGGAC ACAGATTTTT     876

CCACTCCCAA GTCTGGCTGC TTTTTACTTC ACTGTGAGGG GTAAAGGTAA ATCAGCTGTT     936

TTCTTTGTTC AGAAACTCTC TCCAACTTTG CACTTTTCTT AAAG GAA AGT AAT GGA     992
                                               Glu Ser Asn Gly
                                                         1

CCA GTG AAG GTG TGG GGA AGC ATT AAA NGA STG ACT GAA RRC CTG CRT     1040
Pro Val Lys Val Trp Gly Ser Ile Lys Xaa Xaa Thr Glu Xaa Leu Xaa
 5              10              15                  20

GGA TTC CAT GTT CAT GAG TTT GGA GAT AAT ACA GCA G GTCGGGTGTT        1087
Gly Phe His Val His Glu Phe Gly Asp Asn Thr Ala
             25                  30

GTGTTTCTTT TTAGAATGTA TTTGGGAACT TTAATTCATA ATTTAGCTTT TTTTTCTTCT    1147

TCTTATAAAT A GGC TGT ACC AGT GCA GGT CCT CAC TTT AAT CCT CTA TCC    1197
             Gly Cys Thr Ser Ala Gly Pro His Phe Asn Pro Leu Ser
              1               5                  10

AGA AAA CAC GGT GGG CCA AAG GAT GAA GAG AGG T AACAAGATGC             1241
Arg Lys His Gly Gly Pro Lys Asp Glu Glu Arg
 15                  20

TTAACTCTTG TAATAATGGC CGATCATGGT TCTGGAGTTC ATATGGTATA CTACTTGTAA    1301

ATATGTGCTA AGATAATTCC GTGTTTCCCC CACCTTTGCT TTTGAACTTG CTGACTCATC    1361

TAAACCCTGC TCCCAAATGC TGGAATGCTT TTACTTCCTG GCTTAAAGG AATTGACAAA     1421

TGGGCACTTA AAACGATTTG GTTTTGTAGC ATTTGATTGA ATATAGAACT AATACAAGTG    1481

CCAAAGGGGA ACTAATACAG GAAATGTTCA TGAACAGTAC TGTCAACCAC TAGCAAAATC    1541

AATCATCATT GTACTTCTGA AATCAGGTGC AGCCCCATCT TCTTCCCAG AGCATTAGTG     1601

TGTAGACGTG AAGCCTTGTT TGAAGAGCTG TATTTAGAAT GCCTAGCTAC TTGTTTGCAA    1661

ATTTGTGTCC TACTCAGTCA AGTTTTAATT TAGCTCATGA ACTACCTTGA TGTTTAGTGG    1721

CATCAGCCCT AATCCATCTG ATGCTTTTTC ATTATTAGG CAT GTT GGA GAC TTG      1775
                                             His Val Gly Asp Leu
```

```
                                1              5
SGC AAT GTG ACT GCT GAC AAA GAT KST GTG GCC GAT GTG TCT ATT GRA      1823
Xaa Asn Val Thr Ala Asp Lys Asp Xaa Val Ala Asp Val Ser Ile Xaa
                10              15                  20

GAT TCT GTG ATC TCA STC TCA GGA GAC CAT TGC ATC AYT GGC CGC ACA      1871
Asp Ser Val Ile Ser Xaa Ser Gly Asp His Cys Ile Xaa Gly Arg Thr
            25              30                  35

CTG GTG G TAAGTTTTCA TAAAAGGATA TGCATAAAAC TTCTTCTAAC ATACAGTCAT     1928
Leu Val

GTATCTTTTC ACTTTGATTG TTAGTCGCGG TTTCTAAGAT CCAGATAAAC TGTGAAAAAG    1988

CTTTGAGTAG TAGTTTCTAC TTTTAAACTA CTAAATATTA GTATATCTCT CTACTAGGAT    2048

TAATGTTATT TTTCTAATAT TATGAGGTTC TTAAACATCT TTTGGGTATT GTTGGGAGGA    2108

GGTAGTGATT ACTTGACAGC CCAAAGTTAT CTTCTTAAAA TTTTTTACAG GTC CAT      2164
                                                         Val His
                                                           1

GAA AAA GCA GAT GAC TTG GGC AAA GGT GGA AAT GAA GAA AGT ACA AAG      2212
Glu Lys Ala Asp Asp Leu Gly Lys Gly Gly Asn Glu Glu Ser Thr Lys
        5               10              15

ACA GGA AAC GAT GGA AGT CGT TYG RCT TGT GGT GTA ATT GGG ATC GCC      2260
Thr Gly Asn Asp Gly Ser Arg Xaa Xaa Cys Gly Val Ile Gly Ile Ala
        20              25              30

CAA T AAACATTCCC TTGGATGTAG TCTGAGGCCC CTTAACTCAT CTGTTATCCT         2314
Gln
 35

GCTAGCTGTA GAAATGTATC CTGATAAACA TTAAACACTG TAATCTTAAA AGTGTAATTG    2374

TGTGACTTTT TCAGAGTTGC TTTAAAGTAC CTGTAGTGAG AAACTGATTT ATGATCACTT    2434

GGAAGATTTG TATAGTTTTA TAAAACTCAG TTAAAATGTC TGTTTCAATG ACCTGTATTT    2494

TGCCAGACTT AAATCACAGA TGGGTATTAA ACTTGTCAGA ATTTCTTTGT CATTCAAGCC    2554

TGTGAATAAA AACCCTGTAT GGCACTTATT ATGAGGCTAT TAAAAGAATC CAAATTCAAA    2614

CTAAATTAGC TCTGATACTT ATTTATATAA ACTGCTTCAG TGGAACAGAT TTAGTAATAC    2674

TAACAGTGAT AGCATTTTAT TTTGAAAGTG TTTTGAGACC ATCAAAATGC ATACTTTAAA    2734

ACAGCAGGTC TTTTAGCTAA AACTAACACA ACTCTGCTTA GACAAATAGG CTGTCCTTTG    2794

AAGCTT                                                              2800

(2) INFORMATION FOR SEQ ID NO:2:

(i) SEQUENCE CHARACTERISTICS:
        (A) LENGTH: 977 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CCGCCGGCGC GCAGGAGCGG CACTCGTGGC TGTGGTGGCT TCGGCAGCGG CTTCAGCAGA      60

TCGGCGGCAT CAGCGGTACG ACCAGCACTA GCAGC ATG TTG AGC CGG GCA GTG       113
                                      Met Leu Ser Arg Ala Val
                                                            40

TGC GGC ACC AGC AGG CAG CTG GCT CCG GCT TTG GGG TAT CTG GGC TCC      161
Cys Gly Thr Ser Arg Gln Leu Ala Pro Ala Leu Gly Tyr Leu Gly Ser
            45              50              55

AGG CAG AAG CAC AGC CTC CCC GAC CTG CCC TAC GAC TAC GGC GCC CTG      209
Arg Gln Lys His Ser Leu Pro Asp Leu Pro Tyr Asp Tyr Gly Ala Leu
        60              65              70
```

```
GAA CCT CAC ATC AAC GCG CAG ATC ATG CAG CTG CAC CAC AGC AAG CAC       257
Glu Pro His Ile Asn Ala Gln Ile Met Gln Leu His His Ser Lys His
    75                  80                  85

CAC GCG GCC TAC GTG AAC AAC CTG AAC GTC ACC GAG GAG AAG TAC CAG       305
His Ala Ala Tyr Val Asn Asn Leu Asn Val Thr Glu Glu Lys Tyr Gln
 90                  95                 100                 105

GAG GCG TTG GCA AAG GGA GAT GTT ACA GCC CAG ACA GCT CTT CAG CCT       353
Glu Ala Leu Ala Lys Gly Asp Val Thr Ala Gln Thr Ala Leu Gln Pro
                110                 115                 120

GCA CTG AAG TTC AAT GGT GGT GGT CAT ATC AAT CAT AGC ATT TTC TGG       401
Ala Leu Lys Phe Asn Gly Gly Gly His Ile Asn His Ser Ile Phe Trp
            125                 130                 135

ACA AAC CTC AGC CCT AAC GGT GGT GGA GAA CCC AAA GGG GAG TTG CTG       449
Thr Asn Leu Ser Pro Asn Gly Gly Gly Glu Pro Lys Gly Glu Leu Leu
        140                 145                 150

GAA GCC ATC AAA CGT GAC TTT GGT TCC TTT GAC AAG TTT AAG GAG AAG       497
Glu Ala Ile Lys Arg Asp Phe Gly Ser Phe Asp Lys Phe Lys Glu Lys
    155                 160                 165

CTG ACG GCT GCA TCT GTT GGT GTC CAA GGC TCA GGT TGG GGT TGG CTT       545
Leu Thr Ala Ala Ser Val Gly Val Gln Gly Ser Gly Trp Gly Trp Leu
170                 175                 180                 185

GGT TTC AAT AAG GAA CGG GGA CAC TTA CAA ATT GCT GCT TGT CCA AAT       593
Gly Phe Asn Lys Glu Arg Gly His Leu Gln Ile Ala Ala Cys Pro Asn
                190                 195                 200

CAG GAT CCA CTG CAA GGA ACA ACA GGC CTT ATT CCA CTG CTG GGG ATT       641
Gln Asp Pro Leu Gln Gly Thr Thr Gly Leu Ile Pro Leu Leu Gly Ile
            205                 210                 215

GAT GTG TGG GAG CAC GCT TAC TAC CTT CAG TAT AAA AAT GTC AGG CCT       689
Asp Val Trp Glu His Ala Tyr Tyr Leu Gln Tyr Lys Asn Val Arg Pro
        220                 225                 230

GAT TAT CTA AAA GCT ATT TGG AAT GTA ATC AAC TGG GAG AAT GTA ACT       737
Asp Tyr Leu Lys Ala Ile Trp Asn Val Ile Asn Trp Glu Asn Val Thr
    235                 240                 245

GAA AGA TAC ATG GCT TGC AAA AAG T AAACCACGAT CGTTATGCTG                782
Glu Arg Tyr Met Ala Cys Lys Lys
250                 255

AGTATGTTAA GCTCTTTATG ACTGTTTTTG TAGTGGTATA GAGTACTGCA GAATACAGTA     842

AGCTGCTCTA TTGTAGCATT TCTTGATGTT GCTTAGTCAC TTATTTCATA AACAACTTAA     902

TGTTCTGAAT AATTTCTTAC TAAACATTTT GTTATTGGGC AAGTGATTGA AAATAGTAAA     962

TGCTTTGTGT GATTG                                                      977

(2) INFORMATION FOR SEQ ID NO:3:

(i) SEQUENCE CHARACTERISTICS:
        (A) LENGTH: 1389 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

CTGGGTGCAG CTCTCTTTTC AGGAGAGAAA GCTCTCTTGG AGGAGCTGGA AAGGTGCCCG      60

ACTCCAGCC ATG CTG GCG CTA CTG TGT TCC TGC CTG CTC CTG GCA GCC         108
           Met Leu Ala Leu Leu Cys Ser Cys Leu Leu Leu Ala Ala
               225                 230                 235

GGT GCC TCG GAC GCC TGG ACG GGC GAG GAC TCG GCG GAG CCC AAC TCT       156
Gly Ala Ser Asp Ala Trp Thr Gly Glu Asp Ser Ala Glu Pro Asn Ser
            240                 245                 250
```

-continued

```
GAC TCG GCG GAG TGG ATC CGA GAC ATG TAC GCC AAG GTC ACG GAG ATC      204
Asp Ser Ala Glu Trp Ile Arg Asp Met Tyr Ala Lys Val Thr Glu Ile
            255                 260                 265

TGG CAG GAG GTC ATG CAG CGG CGG GAC GAC GAC GGC ACG CTC CAC GCC      252
Trp Gln Glu Val Met Gln Arg Arg Asp Asp Asp Gly Thr Leu His Ala
            270                 275                 280

GCC TGC CAG GTG CAG CCG TCG GCC ACG CTG GAC GCC GCG CAG CCC CGG      300
Ala Cys Gln Val Gln Pro Ser Ala Thr Leu Asp Ala Ala Gln Pro Arg
    285                 290                 295

GTG ACC GGC GTC GTC CTC TTC CGG CAG CTT GCG CCC CGC GCC AAG CTC      348
Val Thr Gly Val Val Leu Phe Arg Gln Leu Ala Pro Arg Ala Lys Leu
300                 305                 310                 315

GAC GCC TTC TTC GCC CTG GAG GGC TTC CCG ACC GAG CCG AAC AGC TCC      396
Asp Ala Phe Phe Ala Leu Glu Gly Phe Pro Thr Glu Pro Asn Ser Ser
                320                 325                 330

AGC CGC GCC ATC CAC GTG CAC CAG TTC GGG GAC CTG AGC CAG GGC TGC      444
Ser Arg Ala Ile His Val His Gln Phe Gly Asp Leu Ser Gln Gly Cys
            335                 340                 345

GAG TCC ACC GGG CCC CAC TAC AAC AAG CTG GCC GTG CCG CAC CCG CAG      492
Glu Ser Thr Gly Pro His Tyr Asn Lys Leu Ala Val Pro His Pro Gln
            350                 355                 360

CAC CCG GGC GAC TTC GGC AAC TTC GCG GTC CGC GAC GGC AGC CTC TGG      540
His Pro Gly Asp Phe Gly Asn Phe Ala Val Arg Asp Gly Ser Leu Trp
            365                 370                 375

AGG TAC CGC GCC GGC CTG GCC GCC TCG CTC GCG GGC CCG CAC TCC ATC      588
Arg Tyr Arg Ala Gly Leu Ala Ala Ser Leu Ala Gly Pro His Ser Ile
380                 385                 390                 395

GTG GGC CGG GCC GTG GTC GTC CAC GCT GGC GAG GAC GAC CTG GGC CGC      636
Val Gly Arg Ala Val Val Val His Ala Gly Glu Asp Asp Leu Gly Arg
                400                 405                 410

GGC GGC AAC CAG GCC AGC GTG GAG AAC GGG AAC GCG GGC CGG CGG CTG      684
Gly Gly Asn Gln Ala Ser Val Glu Asn Gly Asn Ala Gly Arg Arg Leu
            415                 420                 425

GCC TGC TGC GTG GTG GGC GTG TGC GGG CCC GGG CTC TGG GAG CGC CAG      732
Ala Cys Cys Val Val Gly Val Cys Gly Pro Gly Leu Trp Glu Arg Gln
            430                 435                 440

GCG CGG GAG CAC TCA GAG CGC AAG AAG CGG CGG CGC GAG AGC GAG TGC      780
Ala Arg Glu His Ser Glu Arg Lys Lys Arg Arg Arg Glu Ser Glu Cys
            445                 450                 455

AAG GCC GCC T GAGCGCGGCC CCCACCCGGC GGCGGCCAGG GACCCCCGAG            830
Lys Ala Ala
460

GCCCCCCTCT GCCTTTGAGC TTCTCCTCTG CTCCAACAGA CACCTTCCAC TCTGAGGTCT    890

CACCTTCGCC TCTGCTGAAG TCTCCCCGCA GCCCTCTCCA CCCAGAGGTC TCCCTATACC    950

GAGACCCACC ATCCTTCCAT CCTGAGGACC GCCCCAACCC TCGGAGCCCC CCACTCAGTA    1010

GGTCTGAAGG CCTCCATTTG TACCGAAACA CCCCGCTCAC GCTGACAGCC TCCTAGGCTC    1070

CCTGAGGTAC CTTTCCACCC AGACCCTCCT TCCCCACCCC ATAAGCCCTG AGACTCCCGC    1130

CTTTGACCTG ACGATCTTCC CCCTTCCCGC CTTCAGGTTC CTCCTAGGCG CTCAGAGGCC    1190

GCTCTGGGGG GTTGCCTCGA GTCCCCCCAC CCCTCCCCAC CCACCACCGC TCCCGCGGCA    1250

AGCCAGCCCG TGCAACGGAA GCCAGGCCAA CTGCCCCGCG TCTTCAGCTG TTTCGCATCC    1310

ACCGCCACCC CACTGAGAGC TGCTCCTTTG GGGGAATGTT TGGCAACCTT TGTGTTACAG    1370

ATTAAAAATT CAGCAATTC                                                 1389
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ATAAAGTAGT CGCGGAGACG G                                              21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GCCTTCTGCT CGAAATTGAT G                                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ACTCTCTCCA ACTTTGCACT T                                              21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CCCACCTGCT GTATTATCTC C                                              21

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GAATGTATTT GGGAACTTTA ATTC                                           24

(2) INFORMATION FOR SEQ ID NO:9:

(i) SEQUENCE CHARACTERISTICS:
        (A) LENGTH: 24 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:9:

TAGATGAGTC AGCAAGTTCA AAAG                                                24

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CATATAGGCA TGTTGGAGAC T                                                   21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GAAAGATACA TGACTGTACT G                                                   21

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GTATTGTTGG GAGGAGGTAG TGAT                                                24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GCAGGATAAC AGATGAGTTA AGGG                                                24

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GCAACATCAA GAAATGCTAC                                           20

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GGCACTCGTG GCTGTGGTGG CTTC                                      24

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

CACAAAGGTA GCCAAACATT C                                         21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GTGCAGCTCT CTTTTCAGGA G                                         21

(2) INFORMATION FOR SEQ ID NO:18:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

Glu Ser Asn Gly Pro Val Lys Val Trp Gly Ser Ile Lys Gly Leu Thr
1               5                   10                  15
Glu Gly Leu His Gly Phe His Val His Glu Phe Gly Asp Asn Thr Ala
            20                  25                  30

(2) INFORMATION FOR SEQ ID NO:19:

(i) SEQUENCE CHARACTERISTICS:
        (A) LENGTH: 29 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

Gly Asp Thr Val Val Val Thr Gly Ser Ile Thr Gly Leu Thr Glu Gly
1               5                   10                  15

His Gly Phe His Val His Gln Phe Gly Asp Asn Thr Gln
            20                  25

(2) INFORMATION FOR SEQ ID NO:20:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

Gly Glu Lys Thr Val Leu Val Thr Gly Thr Ile Lys Gly Leu Ala Glu
1               5                   10                  15

Gly Asp His Gly Phe His Val His Gln Phe Gly Asp Asn Thr Gln
            20                  25                  30

(2) INFORMATION FOR SEQ ID NO:21:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:21:

Ala Ser Gly Glu Pro Val Val Leu Ser Gly Gln Ile Thr Gly Leu Thr
1               5                   10                  15

Glu Gly Gln His Gly Phe His Val His Gln Tyr Gly Asp Asn Thr Gln
            20                  25                  30

(2) INFORMATION FOR SEQ ID NO:22:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:22:

Gly Asn Ala Asn Ala Val Gly Lys Gly Ile Ile Leu Lys Gly Leu Thr
1               5                   10                  15

Pro Gly Glu His Gly Phe His Val His Gly Phe Gly Asp Asn Thr Asn
            20                  25                  30

(2) INFORMATION FOR SEQ ID NO:23:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:23:

```
Ser Ser Gly Thr Pro Val Lys Val Ser Gly Glu Val Cys Gly Leu Ala
1               5                   10                  15

Lys Gly Leu His Gly Phe His Val His Glu Phe Gly Asp Asn Thr Asn
                20                  25                  30
```

(2) INFORMATION FOR SEQ ID NO:24:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:24:

```
Lys Glu Gly Leu Pro Thr Thr Val Thr Gly Glu Val Lys Gly Leu Thr
1               5                   10                  15

Pro Gly Leu His Gly Phe His Ile His Gln Tyr Gly Asp Thr Thr Asn
                20                  25                  30
```

(2) INFORMATION FOR SEQ ID NO:25:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:25:

```
Gly Val Ala Pro Thr Thr Val Asn Gly Asn Ile Ser Gly Leu Lys Pro
1               5                   10                  15

Gly Leu His Gly Phe His Val His Ala Leu Gly Asp Thr Thr Asn
                20                  25                  30
```

(2) INFORMATION FOR SEQ ID NO:26:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:26:

```
Asp Asp Gly Pro Thr Thr Val Asn Val Arg Ile Ser Gly Leu Ala Pro
1               5                   10                  15

Gly Lys His Gly Phe His Leu His Glu Phe Gly Asp Thr Thr Asn
                20                  25                  30
```

(2) INFORMATION FOR SEQ ID NO:27:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:27:

```
Ser Glu Ser Glu Pro Thr Thr Val Ser Tyr Glu Ile Ala Gly Asn Ser
1               5                   10                  15
```

```
Pro Asn Ala Glu Arg Gly Phe His Ile His Glu Phe Gly Asp Ala Thr
            20                  25                  30
Asn
```

(2) INFORMATION FOR SEQ ID NO:28:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:28:

```
His Val Gly Asp Leu Gly Asn Val Thr Ala Asp Lys Asp Gly Val Ala
1               5                   10                  15
Asp Val Ser Ile Glu Asp Ser Val Ile Ser Leu Ser Gly Asp His Cys
            20                  25                  30
Ile Ile Gly Arg Thr Leu Val
        35
```

(2) INFORMATION FOR SEQ ID NO:29:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:29:

```
His Val Gly Asp Leu Gly Asn Val Thr Ala Asp Lys Asn Gly Val Ala
1               5                   10                  15
Ile Val Asp Ile Val Asp Pro Leu Ile Ser Leu Ser Gly Glu Tyr Ser
            20                  25                  30
Ile Ile Gly Arg Thr Met Val
        35
```

(2) INFORMATION FOR SEQ ID NO:30:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:30:

```
His Val Gly Asp Leu Gly Asn Val Thr Ala Gly Lys Asp Gly Val Ala
1               5                   10                  15
Thr Val Tyr Ile Glu Asp Ser Val Ile Ala Leu Ser Gly Asp His Ser
            20                  25                  30
Ile Ile Gly Arg Thr Met Val
        35
```

(2) INFORMATION FOR SEQ ID NO:31:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:31:

His Val Gly Asp Leu Gly Asn Val Thr Ala Gly Lys Asp Gly Val Ala
1               5                   10                  15

Asn Val Ser Ile Glu Asp Arg Val Ile Ser Leu Ser Gly Glu His Ser
            20                  25                  30

Ile Ile Gly Arg Thr Met Val
            35

(2) INFORMATION FOR SEQ ID NO:32:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:32:

His Val Gly Asp Leu Gly Asn Val Thr Ala Asp Ala Asn Gly Val Ala
1               5                   10                  15

Lys Ile Asp Ile Thr Asp Lys Ile Ser Leu Thr Gly Pro Tyr Ser Ile
            20                  25                  30

Ile Gly Arg Thr Met Val
            35

(2) INFORMATION FOR SEQ ID NO:33:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:33:

His Leu Gly Asp Leu Gly Asn Ile Glu Ala Thr Gly Asp Cys Pro Thr
1               5                   10                  15

Lys Val Asn Ile Thr Asp Ser Lys Ile Thr Leu Phe Gly Ala Asp Ser
            20                  25                  30

Ile Ile Gly Arg Thr Val Val
            35

(2) INFORMATION FOR SEQ ID NO:34:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:34:

His Val Gly Asp Leu Gly Asn Ile Glu Ala Gly Ala Asp Gly Thr Ala
1               5                   10                  15

His Ile Ser Ile Ser Asp Gln His Ile Gln Leu Leu Gly Pro Asn Ser
            20                  25                  30

Ile Ile Gly Arg Ser Ile Val
            35

(2) INFORMATION FOR SEQ ID NO:35:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:35:

```
Glu Ala Gly Asp Leu Gly Asn Ile Thr Val Gly Glu Asp Gly Thr Ala
1               5                  10                  15

Ser Phe Thr Ile Thr Asp Lys Gln Ile Pro Leu Thr Gly Pro Gln Ser
            20                  25                  30

Ile Ile Gly Arg Ala Val Val
        35
```

(2) INFORMATION FOR SEQ ID NO:36:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:36:

```
His Ala Gly Asp Leu Gly Asn Ile Val Ala Asn Thr Asp Gly Val Ala
1               5                  10                  15

Glu Ala Thr Ile Val Asp Asn Gln Ile Pro Leu Thr Gly Pro Asn Ser
            20                  25                  30

Val Val Gly Arg Ala Leu Val
        35
```

(2) INFORMATION FOR SEQ ID NO:37:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:37:

```
His Val Gly Asp Met Gly Asn Val Lys Thr Asp Glu Asn Gly Val Ala
1               5                  10                  15

Lys Gly Ser Phe Lys Asp Ser Leu Ile Lys Leu Ile Gly Pro Thr Ser
            20                  25                  30

Val Val Gly Arg Ser Val Val
        35
```

(2) INFORMATION FOR SEQ ID NO:38:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:38:

```
Met Ala Thr Lys Ala Val Cys Val Leu Lys Gly Asp Gly Pro Val Gln
1               5                   10                  15

Gly Ile Ile Asn Phe Glu Gln Lys
            20
```

(2) INFORMATION FOR SEQ ID NO:39:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:39:

```
Met Ala Thr Lys Ala Val Cys Val Leu Lys Gly Asp Gly Pro Val Gln
1               5                   10                  15

Gly Thr Ile His Phe Glu Ala Lys
            20
```

(2) INFORMATION FOR SEQ ID NO:40:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:40:

```
Ala Thr Lys Ala Val Cys Val Leu Lys Gly Asp Gly Pro Val Gln Gly
1               5                   10                  15

Thr Ile Tyr Phe Glu Leu Lys
            20
```

(2) INFORMATION FOR SEQ ID NO:41:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:41:

```
Met Ala Met Lys Ala Val Cys Val Leu Lys Gly Asp Gly Pro Val Gln
1               5                   10                  15

Gly Thr Ile His Phe Glu Gln Lys
            20
```

(2) INFORMATION FOR SEQ ID NO:42:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:42:

```
Val Lys Ala Val Cys Val Leu Ala Gly Ser Gly Asp Val Lys Gly Val
1               5                   10                  15
```

```
Val Arg Phe Glu Gln Gln
            20

(2) INFORMATION FOR SEQ ID NO:43:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:43:

Val Leu Lys Ala Val Cys Val Leu Arg Gly Ala Gly Glu Thr Thr Gly
1               5                   10                  15

Thr Val Tyr Phe Glu Gln Glu
            20

(2) INFORMATION FOR SEQ ID NO:44:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:44:

Met Val Val Lys Ala Val Cys Val Ile Asn Gly Asp Ala Lys Gly Gly
1               5                   10                  15

Thr Val Phe Phe Glu Gln Glu
            20

(2) INFORMATION FOR SEQ ID NO:45:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:45:

Met Val Lys Ala Val Ala Val Leu Asn Ser Ser Glu Gly Val Ser Gly
1               5                   10                  15

Thr Tyr Leu Phe Thr Gln Val
            20

(2) INFORMATION FOR SEQ ID NO:46:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:46:

Ala Thr Lys Lys Ala Val Ala Val Leu Leu Gly Thr Ser Asn Val Glu
1               5                   10                  15

Gly Val Val Thr Leu Thr Gln Glu
            20
```

(2) INFORMATION FOR SEQ ID NO:47:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:47:

```
Met Val Lys Ala Val Ala Val Leu Ala Gly Thr Asp Val Lys Gly Thr
1               5                   10                  15

Ile Phe Phe Ser Gln Glu
            20
```

(2) INFORMATION FOR SEQ ID NO:48:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:48:

```
Met Val Lys Ala Val Ala Val Val Arg Gly Asp Ser Asn Val Lys Gly
1               5                   10                  15

Thr Val Ile Phe Glu Gln Glu
            20
```

(2) INFORMATION FOR SEQ ID NO:49:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:49:

```
Val Gln Ala Val Ala Val Leu Lys Gly Asp Ala Gly Val Ser Gly Val
1               5                   10                  15

Val Lys Phe Glu Gln Ala
            20
```

(2) INFORMATION FOR SEQ ID NO:50:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

```
GATGAAGAGA GGTAACAAGA TGCTTAACTC TTGTAATAAT GGCGWTACGT TTCTGGAGTT    60
C                                                                    61
```

(2) INFORMATION FOR SEQ ID NO:51:

(i) SEQUENCE CHARACTERISTICS:

(A) LENGTH: 154 amino acids
          (B) TYPE: amino acid
          (C) STRANDEDNESS: Not Relevant
          (D) TOPOLOGY: linear (ii) MOLECULE TYPE: protein (ix) FEATURE:
          (D) OTHER INFORMATION: Xaa at position 5 is Ala or Val.
              Xaa at position 38 is Gly or Arg. Xaa at position 39 is
              Leu or Val. Xaa at position 42 is Gly, Ser or Asp. Xaa
              at position 44 is His or Arg. Xaa at position 86 is Gly
              or Arg. Xaa at position 94 is Gly, Cys or Ala. Xaa at
              position 101 is Gly or Glu. Xaa at position 107 is Leu
              or Val. Xaa at position 114 is Ile or Thr. Xaa at
              position 145 is Leu or Ser. Xaa at position 146 is Ala
              or Thr.

(xi) SEQUENCE DESCRIPTION: SEQ ID NO:51:

Met Ala Thr Lys Xaa Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Xaa Xaa Thr Glu Xaa Leu Xaa Gly Phe His Val
            35                  40                  45

His Glu Phe Gly Asp Asn Thr Ala Gly Cys Thr Ser Ala Gly Pro His
50                  55                  60

Phe Asn Pro Leu Ser Arg Lys His Gly Pro Lys Asp Glu Glu Arg
65                  70                  75                  80

His Val Gly Asp Leu Xaa Asn Val Thr Ala Asp Lys Asp Xaa Val Ala
                85                  90                  95

Asp Val Ser Ile Xaa Asp Ser Val Ile Ser Xaa Ser Gly Asp His Cys
                100                 105                 110

Ile Xaa Gly Arg Thr Leu Val Val His Glu Lys Ala Asp Asp Leu Gly
    115                 120                 125

Lys Gly Gly Asn Glu Glu Ser Thr Lys Thr Gly Asn Asp Gly Ser Arg
    130                 135                 140

Xaa Xaa Cys Gly Val Ile Gly Ile Ala Gln
145                 150

(2) INFORMATION FOR SEQ ID NO:52:

(i) SEQUENCE CHARACTERISTICS:
          (A) LENGTH: 222 amino acids
          (B) TYPE: amino acid
          (D) TOPOLOGY: linear (ii) MOLECULE TYPE: protein (xi) SEQUENCE DESCRIPTION: SEQ ID NO:52:

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
                20                  25                  30

Tyr Asp Tyr Gly Ala Leu Glu Pro His Ile Asn Ala Gln Ile Met Gln
            35                  40                  45

Leu His His Ser Lys His His Ala Ala Tyr Val Asn Asn Leu Asn Val
        50                  55                  60

Thr Glu Glu Lys Tyr Gln Glu Ala Leu Ala Lys Gly Asp Val Thr Ala
65                  70                  75                  80

Gln Thr Ala Leu Gln Pro Ala Leu Lys Phe Asn Gly Gly Gly His Ile
                85                  90                  95

```
Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
            115                 120                 125

Asp Lys Phe Lys Glu Lys Leu Thr Ala Ala Ser Val Gly Val Gln Gly
130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
            195                 200                 205

Asn Trp Glu Asn Val Thr Glu Arg Tyr Met Ala Cys Lys Lys
            210                 215                 220

(2) INFORMATION FOR SEQ ID NO:53:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO:53:

Met Leu Ala Leu Leu Cys Ser Cys Leu Leu Leu Ala Ala Gly Ala Ser
1               5                   10                  15

Asp Ala Trp Thr Gly Glu Asp Ser Ala Glu Pro Asn Ser Asp Ser Ala
            20                  25                  30

Glu Trp Ile Arg Asp Met Tyr Ala Lys Val Thr Glu Ile Trp Gln Glu
            35                  40                  45

Val Met Gln Arg Arg Asp Asp Gly Thr Leu His Ala Ala Cys Gln
50                  55                  60

Val Gln Pro Ser Ala Thr Leu Asp Ala Ala Gln Pro Arg Val Thr Gly
65                  70                  75                  80

Val Val Leu Phe Arg Gln Leu Ala Pro Arg Ala Lys Leu Asp Ala Phe
            85                  90                  95

Phe Ala Leu Glu Gly Phe Pro Thr Glu Pro Asn Ser Ser Ser Arg Ala
            100                 105                 110

Ile His Val His Gln Phe Gly Asp Leu Ser Gln Gly Cys Glu Ser Thr
            115                 120                 125

Gly Pro His Tyr Asn Lys Leu Ala Val Pro His Pro Gln His Pro Gly
130                 135                 140

Asp Phe Gly Asn Phe Ala Val Arg Asp Gly Ser Leu Trp Arg Tyr Arg
145                 150                 155                 160

Ala Gly Leu Ala Ala Ser Leu Ala Gly Pro His Ser Ile Val Gly Arg
                165                 170                 175

Ala Val Val Val His Ala Gly Glu Asp Asp Leu Gly Arg Gly Gly Asn
            180                 185                 190

Gln Ala Ser Val Glu Asn Gly Asn Ala Gly Arg Arg Leu Ala Cys Cys
            195                 200                 205
```

-continued

```
Val Val Gly Val Cys Gly Pro Gly Leu Trp Glu Arg Gln Ala Arg Glu
    210                 215                 220

His Ser Glu Arg Lys Lys Arg Arg Arg Glu Ser Glu Cys Lys Ala Ala
225                 230                 235                 240
```